United States Patent [19]
Little, II et al.

[11] Patent Number: 5,348,942
[45] Date of Patent: Sep. 20, 1994

[54] THERAPEUTIC USES OF BACTERICIDAL/PERMEABILITY INCREASING PROTEIN PRODUCTS

[75] Inventors: Roger G. Little, II, Benicia; Hélene Gazzano-Santoro, San Bruno; James B. Parent, Oakland, all of Calif.

[73] Assignee: Xoma Corporation, Berkeley, Calif.

[21] Appl. No.: 30,644

[22] Filed: Mar. 12, 1993

[51] Int. Cl.$^5$ .............................................. A61K 37/02
[52] U.S. Cl. ....................................... 514/12; 514/21; 514/13; 514/14; 514/15
[58] Field of Search .................... 514/12, 21; 530/324, 530/350; 435/69.1

[56] References Cited

U.S. PATENT DOCUMENTS

| | | | |
|---|---|---|---|
| 5,086,164 | 2/1992 | Maione et al. | 530/324 |
| 5,112,946 | 5/1992 | Maione | 530/324 |
| 5,171,739 | 12/1992 | Scott et al. | 514/12 |

FOREIGN PATENT DOCUMENTS

WO92/01003 1/1992 PCT Int'l Appl. .
WO92/02240 2/1992 PCT Int'l Appl. .
WO93/13794 7/1993 PCT Int'l Appl. .

OTHER PUBLICATIONS

Mannion et al. Mar. 1990. J. Clin Invest. 85:853–860.
Weiss et al. 1978. J. Biol. Chem. 253(8): 2664–2672.
Charles, et al., *J. Biol. Chem.*, "The Three-dimensional Structure of Bovine Platelet Factor 4 at 3.0–Å Resolution," 264(4): 2092–2099 (Feb. 5, 1989).
Cook, et al., *Circulation*, "Platelet Factor 4 Efficiently Reverses Heparin Anticoagulation in the Rat Without Adverse Effects of Heparin–Protamine Complexes," 85(3): 1102–1109 (Mar. 1992).
Elsbach, et al., *J. Biol. Chem.*, "Separation and Purification of a Potent Bactericidal/Permeability–increasing Protein and a Closely Associated Pospholipase A$_2$ from Rabbit Polymorphonuclear Leukocytes," 254(21): 11000–11009 (Nov. 10, 1979).
Folkman, et al., *Inflammation: Basic Principles and Clinical Correlates*, "Angiogenesis and Inflammation," 2nd Ed. Chapter 40, pp. 821–839 (1992).
Gammon, et al., *J. Exp. Med*, "T Cell Determinant Structure: Cores and Determinant Envelopes in Three Mouse Major Histocompatibility Complex Haplotypes," 173: 609–617 (Mar. 1991).
Garcia, et al., *BioWorld Today*, "Repligen IND for Platelet Factor" p. 5 (Jan. 11, 1983).
Gazzano–Santoro, et al., *Infect. Immunol.*, "High–Affinity Binding of the Bactericidal/Permeability Increasing Protein and a Recombinant Amino–Terminal Fragment to the Lipid A Region of Lipopolysaccharide," 60(11):4754–4761 (Nov., 1992).
Gray, et al., *J. Biol. Chem.*, "Cloning of the cDNA of a Human Neutrophil Bactericidal Protein," 264(16): 9505–9509 (Jun. 5, 1989).
Heyderman, et al., *Thrombosis Res.*, "Reduction of the Anticoagulant Activity of Glycosaminoglycans on the Surface of the Vascular Endothelium by Endotoxin and Neutrophils: Evaluation by an Amidolytic Assay," 67:677–685 (Apr. 28, 1992).
Hiti-Harper, et al., *Science,*. "Platelet Factor 4: An Inhibitor of Collagenase," 199:991–992 (Mar. 3, 1978).
Maeji, et al., *J. Immunological Methods*, "Multi–pin peptide strategy for T cell determinant analysis," 134:23–33 (1990).
Maione , et al., *Cancer Res.*, "Inhibition of Tumor Growth in Mice by an Analogue of Platelet Factor 4 That Lacks Affinity for Heparin and Retains Potent (List continued on next page.)

Primary Examiner—Keith C. Furman
Attorney, Agent, or Firm—Marshall, O'Toole, Gerstein, Murray & Borun

[57] ABSTRACT

The present invention provides therapeutic methods for treatment of conditions including the neutralization of the anti-coagulant activity of heparin, inhibition of angiogenesis, tumor and endothelial cell proliferation, and treatment of chronic inflammatory diseases by administration of bactericidal/permeability-increasing (BPI) protein products.

2 Claims, 8 Drawing Sheets

OTHER PUBLICATIONS

Angiostatic Activity," 51:2077–2083 (Apr. 15, 1991).

Maione, et al., *CAS BioTech Updates–Antibody Conjugates,* p. 1, 1334, 117:226303x Issue Jun. 26, 1992).

Miles, et al., VII *International Conference on Aids,* Florence, Italy, "Recombinant Platelet Factor 4 (rPF4) and a Non–heparin Binding Derivative Inhibit Aids–Kaposi Sarcoma Derived Cell Lines," Paper 41(8), W.A. 1066, p. 108 (Jun. 16–21, 1991).

Peacock, et al., *J. Exp. Med.*, "Angiogenesis Inhibition Suppresses Collagen Arthritis," 175: 1135–1138 (Apr., 1992).

Repligen Corporation, *Research in Review,* Spring 1992.

Stuart, et al., *J. Clin. Invest.,* "Nature and Specificity of the Immune Response to Collagen in Type II Collagen–induced Arthritis in Mice" 69: 673–683 (Mar., 1982).

Taylor, et al., *Nature,* "Protamine is an inhibitor of angiogenesis," 297: 307–312 (May 27, 1982).

Weiss, et al., *Blood,* "Cellular and Subcellular Localization of the Bactericidal/Permeability–Increasing Protein of Neutrophils," 69(2): 652–659 (Feb., 1987).

Yayon, et al., *Cell,* "Cell Surface, Heparin–like Molecules Are Required for Binding of Basis Fibroblast Growth Factor to Its High Affinity Receptor," 64: 641–648 (Feb. 22, 1991).

Yong, et al., *Microbial Pathogenesis,* "An experimental mouse model of Yersinia–induced reactive arthritis," 4: 305–310 (1988).

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
        ( A ) LENGTH: 1813 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 31..1491

( i x ) FEATURE:
        ( A ) NAME/KEY: matpeptide
        ( B ) LOCATION: 124..1491

( x i ) SEQUENCE DESCRIPTION: SEQ ID NO:1:

```
CAGGCCTTGA GGTTTTGGCA GCTCTGGAGG ATG AGA GAG AAC ATG GCC AGG GGC         54
                                 Met Arg Glu Asn Met Ala Arg Gly
                                 -31 -30                  -25

CCT TGC AAC GCG CCG AGA TGG GTG TCC CTG ATG GTG CTC GTC GCC ATA         102
```

|     |     |     |     |     |     |     |     |     |     |     |     |     |     |     |     |
|---|---|---|---|---|---|---|---|---|---|---|---|---|---|---|---|
| Pro | Cys | Asn | Ala<br>-20 | Pro | Arg | Trp | Val | Ser<br>-15 | Leu | Met | Val | Leu | Val<br>-10 | Ala | Ile |

| GGC | ACC | GCC | GTG | ACA | GCG | GCC | GTC | AAC | CCT | GGC | GTC | GTG | GTC | AGG | ATC | 150 |
|---|---|---|---|---|---|---|---|---|---|---|---|---|---|---|---|---|
| Gly | Thr | Ala<br>-5 | Val | Thr | Ala | Ala | Val | Asn<br>1 | Pro | Gly | Val | Val<br>5 | Val | Arg | Ile |  |

| TCC | CAG | AAG | GGC | CTG | GAC | TAC | GCC | AGC | CAG | CAG | GGG | ACG | GCC | GCT | CTG | 198 |
|---|---|---|---|---|---|---|---|---|---|---|---|---|---|---|---|---|
| Ser<br>10 | Gln | Lys | Gly | Leu | Asp<br>15 | Tyr | Ala | Ser | Gln | Gln<br>20 | Gly | Thr | Ala | Ala | Leu<br>25 |  |

| CAG | AAG | GAG | CTG | AAG | AGG | ATC | AAG | ATT | CCT | GAC | TAC | TCA | GAC | AGC | TTT | 246 |
|---|---|---|---|---|---|---|---|---|---|---|---|---|---|---|---|---|
| Gln | Lys | Glu | Leu | Lys<br>30 | Arg | Ile | Lys | Ile | Pro<br>35 | Asp | Tyr | Ser | Asp | Ser<br>40 | Phe |  |

| AAG | ATC | AAG | CAT | CTT | GGG | AAG | GGG | CAT | TAT | AGC | TTC | TAC | AGC | ATG | GAC | 294 |
|---|---|---|---|---|---|---|---|---|---|---|---|---|---|---|---|---|
| Lys | Ile | Lys | His<br>45 | Leu | Gly | Lys | Gly | His<br>50 | Tyr | Ser | Phe | Tyr | Ser<br>55 | Met | Asp |  |

| ATC | CGT | GAA | TTC | CAG | CTT | CCC | AGT | TCC | CAG | ATA | AGC | ATG | GTG | CCC | AAT | 342 |
|---|---|---|---|---|---|---|---|---|---|---|---|---|---|---|---|---|
| Ile | Arg | Glu<br>60 | Phe | Gln | Leu | Pro | Ser<br>65 | Ser | Gln | Ile | Ser | Met<br>70 | Val | Pro | Asn |  |

| GTG | GGC | CTT | AAG | TTC | TCC | ATC | AGC | AAC | GCC | AAT | ATC | AAG | ATC | AGC | GGG | 390 |
|---|---|---|---|---|---|---|---|---|---|---|---|---|---|---|---|---|
| Val | Gly<br>75 | Leu | Lys | Phe | Ser | Ile<br>80 | Ser | Asn | Ala | Asn | Ile<br>85 | Lys | Ile | Ser | Gly |  |

| AAA | TGG | AAG | GCA | CAA | AAG | AGA | TTC | TTA | AAA | ATG | AGC | GGC | AAT | TTT | GAC | 438 |
|---|---|---|---|---|---|---|---|---|---|---|---|---|---|---|---|---|
| Lys<br>90 | Trp | Lys | Ala | Gln | Lys<br>95 | Arg | Phe | Leu | Lys | Met<br>100 | Ser | Gly | Asn | Phe | Asp<br>105 |  |

| CTG | AGC | ATA | GAA | GGC | ATG | TCC | ATT | TCG | GCT | GAT | CTG | AAG | CTG | GGC | AGT | 486 |
|---|---|---|---|---|---|---|---|---|---|---|---|---|---|---|---|---|
| Leu | Ser | Ile | Glu | Gly<br>110 | Met | Ser | Ile | Ser | Ala<br>115 | Asp | Leu | Lys | Leu | Gly<br>120 | Ser |  |

| AAC | CCC | ACG | TCA | GGC | AAG | CCC | ACC | ATC | ACC | TGC | TCC | AGC | TGC | AGC | AGC | 534 |
|---|---|---|---|---|---|---|---|---|---|---|---|---|---|---|---|---|
| Asn | Pro | Thr | Ser<br>125 | Gly | Lys | Pro | Thr | Ile<br>130 | Thr | Cys | Ser | Ser | Cys<br>135 | Ser | Ser |  |

| CAC | ATC | AAC | AGT | GTC | CAC | GTG | CAC | ATC | TCA | AAG | AGC | AAA | GTC | GGG | TGG | 582 |
|---|---|---|---|---|---|---|---|---|---|---|---|---|---|---|---|---|
| His | Ile | Asn | Ser<br>140 | Val | His | Val | His | Ile<br>145 | Ser | Lys | Ser | Lys | Val<br>150 | Gly | Trp |  |

| CTG | ATC | CAA | CTC | TTC | CAC | AAA | AAA | ATT | GAG | TCT | GCG | CTT | CGA | AAC | AAG | 630 |
|---|---|---|---|---|---|---|---|---|---|---|---|---|---|---|---|---|
| Leu | Ile | Gln<br>155 | Leu | Phe | His | Lys | Lys<br>160 | Ile | Glu | Ser | Ala | Leu<br>165 | Arg | Asn | Lys |  |

| ATG | AAC | AGC | CAG | GTC | TGC | GAG | AAA | GTG | ACC | AAT | TCT | GTA | TCC | TCC | AAG | 678 |
|---|---|---|---|---|---|---|---|---|---|---|---|---|---|---|---|---|
| Met<br>170 | Asn | Ser | Gln | Val | Cys<br>175 | Glu | Lys | Val | Thr | Asn<br>180 | Ser | Val | Ser | Ser | Lys<br>185 |  |

| CTG | CAA | CCT | TAT | TTC | CAG | ACT | CTG | CCA | GTA | ATG | ACC | AAA | ATA | GAT | TCT | 726 |
|---|---|---|---|---|---|---|---|---|---|---|---|---|---|---|---|---|
| Leu | Gln | Pro | Tyr | Phe<br>190 | Gln | Thr | Leu | Pro | Val<br>195 | Met | Thr | Lys | Ile | Asp<br>200 | Ser |  |

| GTG | GCT | GGA | ATC | AAC | TAT | GGT | CTG | GTG | GCA | CCT | CCA | GCA | ACC | ACG | GCT | 774 |
|---|---|---|---|---|---|---|---|---|---|---|---|---|---|---|---|---|
| Val | Ala | Gly | Ile | Asn<br>205 | Tyr | Gly | Leu | Val | Ala<br>210 | Pro | Pro | Ala | Thr | Thr<br>215 | Ala |  |

| GAG | ACC | CTG | GAT | GTA | CAG | ATG | AAG | GGG | GAG | TTT | TAC | AGT | GAG | AAC | CAC | 822 |
|---|---|---|---|---|---|---|---|---|---|---|---|---|---|---|---|---|
| Glu | Thr | Leu | Asp<br>220 | Val | Gln | Met | Lys | Gly<br>225 | Glu | Phe | Tyr | Ser | Glu<br>230 | Asn | His |  |

| CAC | AAT | CCA | CCT | CCC | TTT | GCT | CCA | CCA | GTG | ATG | GAG | TTT | CCC | GCT | GCC | 870 |
|---|---|---|---|---|---|---|---|---|---|---|---|---|---|---|---|---|
| His | Asn<br>235 | Pro | Pro | Pro | Phe | Ala<br>240 | Pro | Pro | Val | Met | Glu<br>245 | Phe | Pro | Ala | Ala |  |

| CAT | GAC | CGC | ATG | GTA | TAC | CTG | GGC | CTC | TCA | GAC | TAC | TTC | TTC | AAC | ACA | 918 |
|---|---|---|---|---|---|---|---|---|---|---|---|---|---|---|---|---|
| His<br>250 | Asp | Arg | Met | Val | Tyr<br>255 | Leu | Gly | Leu | Ser | Asp<br>260 | Tyr | Phe | Phe | Asn | Thr<br>265 |  |

| GCC | GGG | CTT | GTA | TAC | CAA | GAG | GCT | GGG | GTC | TTG | AAG | ATG | ACC | CTT | AGA | 966 |
|---|---|---|---|---|---|---|---|---|---|---|---|---|---|---|---|---|
| Ala | Gly | Leu | Val | Tyr<br>270 | Gln | Glu | Ala | Gly | Val<br>275 | Leu | Lys | Met | Thr | Leu<br>280 | Arg |  |

| GAT | GAC | ATG | ATT | CCA | AAG | GAG | TCC | AAA | TTT | CGA | CTG | ACA | ACC | AAG | TTC | 1014 |
|---|---|---|---|---|---|---|---|---|---|---|---|---|---|---|---|---|
| Asp | Asp | Met | Ile | Pro<br>285 | Lys | Glu | Ser | Lys | Phe<br>290 | Arg | Leu | Thr | Thr | Lys<br>295 | Phe |  |

| TTT | GGA | ACC | TTC | CTA | CCT | GAG | GTG | GCC | AAG | AAG | TTT | CCC | AAC | ATG | AAG | 1062 |
|---|---|---|---|---|---|---|---|---|---|---|---|---|---|---|---|---|
| Phe | Gly | Thr<br>300 | Phe | Leu | Pro | Glu | Val<br>305 | Ala | Lys | Lys | Phe | Pro<br>310 | Asn | Met | Lys |  |

| | | | | | | | | | | | | | | | | |
|---|---|---|---|---|---|---|---|---|---|---|---|---|---|---|---|---|
|ATA|CAG|ATC|CAT|GTC|TCA|GCC|TCC|ACC|CCG|CCA|CAC|CTG|TCT|GTG|CAG|1110|
|Ile|Gln|Ile|His|Val|Ser|Ala|Ser|Thr|Pro|Pro|His|Leu|Ser|Val|Gln||
| |315| | | |320| | | |  |325| | | | | | |
|CCC|ACC|GGC|CTT|ACC|TTC|TAC|CCT|GCC|GTG|GAT|GTC|CAG|GCC|TTT|GCC|1158|
|Pro|Thr|Gly|Leu|Thr|Phe|Tyr|Pro|Ala|Val|Asp|Val|Gln|Ala|Phe|Ala||
|330| | | | |335| | | |340| | | | | |345| |
|GTC|CTC|CCC|AAC|TCC|TCC|CTG|GCT|TCC|CTC|TTC|CTG|ATT|GGC|ATG|CAC|1206|
|Val|Leu|Pro|Asn|Ser|Ser|Leu|Ala|Ser|Leu|Phe|Leu|Ile|Gly|Met|His||
| | | | |350| | | | |355| | | | |360| | |
|ACA|ACT|GGT|TCC|ATG|GAG|GTC|AGC|GCC|GAG|TCC|AAC|AGG|CTT|GTT|GGA|1254|
|Thr|Thr|Gly|Ser|Met|Glu|Val|Ser|Ala|Glu|Ser|Asn|Arg|Leu|Val|Gly||
| | | |365| | | | |370| | | | |375| | | |
|GAG|CTC|AAG|CTG|GAT|AGG|CTG|CTC|CTG|GAA|CTG|AAG|CAC|TCA|AAT|ATT|1302|
|Glu|Leu|Lys|Leu|Asp|Arg|Leu|Leu|Leu|Glu|Leu|Lys|His|Ser|Asn|Ile||
| | |380| | | | |385| | | | |390| | | | |
|GGC|CCC|TTC|CCG|GTT|GAA|TTG|CTG|CAG|GAT|ATC|ATG|AAC|TAC|ATT|GTA|1350|
|Gly|Pro|Phe|Pro|Val|Glu|Leu|Leu|Gln|Asp|Ile|Met|Asn|Tyr|Ile|Val||
| |395| | | | |400| | | | |405| | | | | |
|CCC|ATT|CTT|GTG|CTG|CCC|AGG|GTT|AAC|GAG|AAA|CTA|CAG|AAA|GGC|TTC|1398|
|Pro|Ile|Leu|Val|Leu|Pro|Arg|Val|Asn|Glu|Lys|Leu|Gln|Lys|Gly|Phe||
|410| | | | |415| | | | |420| | | | |425| |
|CCT|CTC|CCG|ACG|CCG|GCC|AGA|GTC|CAG|CTC|TAC|AAC|GTA|GTG|CTT|CAG|1446|
|Pro|Leu|Pro|Thr|Pro|Ala|Arg|Val|Gln|Leu|Tyr|Asn|Val|Val|Leu|Gln||
| | | |430| | | | |435| | | | |440| | | |
|CCT|CAC|CAG|AAC|TTC|CTG|CTG|TTC|GGT|GCA|GAC|GTT|GTC|TAT|AAA| |1491|
|Pro|His|Gln|Asn|Phe|Leu|Leu|Phe|Gly|Ala|Asp|Val|Val|Tyr|Lys| | |
| | | |445| | | | |450| | | | |455| | | |

| | | | | |
|---|---|---|---|---|
|TGAAGGCACC|AGGGGTGCCG|GGGGCTGTCA|GCCGCACCTG|TTCCTGATGG GCTGTGGGGC|1551|
|ACCGGCTGCC|TTTCCCCAGG|GAATCCTCTC|CAGATCTTAA|CCAAGAGCCC CTTGCAAACT|1611|
|TCTTCGACTC|AGATTCAGAA|ATGATCTAAA|CACGAGGAAA|CATTATTCAT TGGAAAAGTG|1671|
|CATGGTGTGT|ATTTTAGGGA|TTATGAGCTT|CTTTCAAGGG|CTAAGGCTGC AGAGATATTT|1731|
|CCTCCAGGAA|TCGTGTTTCA|ATTGTAACCA|AGAAATTTCC|ATTTGTGCTT CATGAAAAAA|1791|
|AACTTCTGGT|TTTTTTCATG|TG| | |1813|

( 2 ) INFORMATION FOR SEQ ID NO:2:

( i ) SEQUENCE CHARACTERISTICS:
        ( A ) LENGTH: 487 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

| | | | | | | | | | | | | | | |
|---|---|---|---|---|---|---|---|---|---|---|---|---|---|---|
|Met|Arg|Glu|Asn|Met|Ala|Arg|Gly|Pro|Cys|Asn|Ala|Pro|Arg|Trp|Val|
|-31|-30| | | | |-25| | | | |-20| | | | |
|Ser|Leu|Met|Val|Leu|Val|Ala|Ile|Gly|Thr|Ala|Val|Thr|Ala|Ala|Val|
|-15| | | |-10| | | | |-5| | | | | |1|
|Asn|Pro|Gly|Val|Val|Val|Arg|Ile|Ser|Gln|Lys|Gly|Leu|Asp|Tyr|Ala|
| | | |5| | | | |10| | | | |15| | |
|Ser|Gln|Gln|Gly|Thr|Ala|Ala|Leu|Gln|Lys|Glu|Leu|Lys|Arg|Ile|Lys|
| | |20| | | | |25| | | | |30| | | |
|Ile|Pro|Asp|Tyr|Ser|Asp|Ser|Phe|Lys|Ile|Lys|His|Leu|Gly|Lys|Gly|
| |35| | | | |40| | | | |45| | | | |
|His|Tyr|Ser|Phe|Tyr|Ser|Met|Asp|Ile|Arg|Glu|Phe|Gln|Leu|Pro|Ser|
|50| | | | |55| | | | |60| | | | |65|
|Ser|Gln|Ile|Ser|Met|Val|Pro|Asn|Val|Gly|Leu|Lys|Phe|Ser|Ile|Ser|
| | | |70| | | | |75| | | | |80| | |

| | | | | | | | | | | | | | |
|---|---|---|---|---|---|---|---|---|---|---|---|---|---|
| Asn | Ala | Asn | Ile 85 | Lys | Ile | Ser | Gly | Lys 90 | Trp | Lys | Ala | Gln | Lys 95 | Arg | Phe |
| Leu | Lys | Met 100 | Ser | Gly | Asn | Phe | Asp 105 | Leu | Ser | Ile | Glu | Met 110 | Ser | Ile |
| Ser | Ala 115 | Asp | Leu | Lys | Leu | Gly 120 | Ser | Asn | Pro | Thr | Ser 125 | Gly | Lys | Pro | Thr |
| Ile 130 | Thr | Cys | Ser | Ser | Cys 135 | Ser | Ser | His | Ile | Asn 140 | Ser | Val | His | Val | His 145 |
| Ile | Ser | Lys | Ser | Lys 150 | Val | Gly | Trp | Leu | Ile 155 | Gln | Leu | Phe | His | Lys 160 | Lys |
| Ile | Glu | Ser | Ala 165 | Leu | Arg | Asn | Lys | Met 170 | Asn | Ser | Gln | Val | Cys 175 | Glu | Lys |
| Val | Thr | Asn 180 | Ser | Val | Ser | Ser | Lys 185 | Leu | Gln | Pro | Tyr | Phe 190 | Gln | Thr | Leu |
| Pro | Val 195 | Met | Thr | Lys | Ile | Asp 200 | Ser | Val | Ala | Gly | Ile 205 | Asn | Tyr | Gly | Leu |
| Val 210 | Ala | Pro | Pro | Ala | Thr 215 | Thr | Ala | Glu | Thr | Leu 220 | Asp | Val | Gln | Met | Lys 225 |
| Gly | Glu | Phe | Tyr | Ser 230 | Glu | Asn | His | His | Asn 235 | Pro | Pro | Pro | Phe | Ala 240 | Pro |
| Pro | Val | Met | Glu 245 | Phe | Pro | Ala | Ala | His 250 | Asp | Arg | Met | Val | Tyr 255 | Leu | Gly |
| Leu | Ser | Asp 260 | Tyr | Phe | Phe | Asn | Thr 265 | Ala | Gly | Leu | Val | Tyr 270 | Gln | Glu | Ala |
| Gly | Val 275 | Leu | Lys | Met | Thr | Leu 280 | Arg | Asp | Asp | Met | Ile 285 | Pro | Lys | Glu | Ser |
| Lys 290 | Phe | Arg | Leu | Thr | Thr 295 | Lys | Phe | Phe | Gly | Thr 300 | Phe | Leu | Pro | Glu | Val 305 |
| Ala | Lys | Lys | Phe | Pro 310 | Asn | Met | Lys | Ile | Gln 315 | Ile | His | Val | Ser | Ala 320 | Ser |
| Thr | Pro | Pro | His 325 | Leu | Ser | Val | Gln | Pro 330 | Thr | Gly | Leu | Thr | Phe 335 | Tyr | Pro |
| Ala | Val | Asp 340 | Val | Gln | Ala | Phe | Ala 345 | Val | Leu | Pro | Asn | Ser 350 | Ser | Leu | Ala |
| Ser | Leu 355 | Phe | Leu | Ile | Gly | Met 360 | His | Thr | Thr | Gly | Ser 365 | Met | Glu | Val | Ser |
| Ala 370 | Glu | Ser | Asn | Arg | Leu 375 | Val | Gly | Glu | Leu | Lys 380 | Leu | Asp | Arg | Leu | Leu 385 |
| Leu | Glu | Leu | Lys | His 390 | Ser | Asn | Ile | Gly | Pro 395 | Phe | Pro | Val | Glu | Leu 400 | Leu |
| Gln | Asp | Ile | Met 405 | Asn | Tyr | Ile | Val | Pro 410 | Ile | Leu | Val | Leu | Pro 415 | Arg | Val |
| Asn | Glu | Lys 420 | Leu | Gln | Lys | Gly | Phe 425 | Pro | Leu | Pro | Thr | Pro 430 | Ala | Arg | Val |
| Gln | Leu 435 | Tyr | Asn | Val | Val | Leu 440 | Gln | Pro | His | Gln | Asn 445 | Phe | Leu | Leu | Phe |
| Gly 450 | Ala | Asp | Val | Val | Tyr 455 | Lys | | | | | | | | | |

THERAPEUTIC USES OF BACTERICIDAL/PERMEABILITY INCREASING PROTEIN PRODUCTS

BACKGROUND OF THE INVENTION

The present invention relates to therapeutic uses of bactericidal/permeability increasing (BPI) protein products for the treatment of conditions not directly associated with gram negative bacterial infection including neutralization of the anti-coagulant properties of heparin, inhibition of angiogenesis, tumor and endothelial cell proliferation and treatment of chronic inflammatory disease states such as arthritis.

HEPARIN BINDING

Heparin is a heterogenous group of straight-chain anionic mucopolysaccharides, called glycosaminoglycans having anticoagulant properties. Although others may be present, the main sugars occurring in heparin are: (1) α-L-iduronic acid 2-sulfate, (2) 2-deoxy-2-sulfamino-α-D-glucose 6-sulfate, (3) β-D-glucoronic acid, (4) 2-acetamido-2-deoxy-α-D-glucose, and (5) α-L-iduronic acid. These sugars are present in decreasing amounts, usually in the order (2)>(1)>(4)>(3)>(5), and are joined by glycosidic linkages, forming polymers of varying sizes. Heparin is strongly acidic because of its content of covalently linked sulfate and carboxylic acid groups. Heparin is found within mast cell granules and is released upon degranulation. A cell associated form of heparin is termed heparan sulfate. Heparan sulfate is a broad term used to describe a variety of sulfated proteoglycans (HSPG's) found with a near-ubiquitous distribution on mammalian cell surface membranes and in the extracellular matrix. HSPG contains a variable percentage of pentameric heparin-like sequences that function in a similar fashion as soluble heparin. The HSPG's serve as a repository for antithrombin III (ATIII) and for heparin-binding growth factors such as fibroblast growth factors (FGF) 1–5, IL-8, GM-CSF and IL-3. Folkman et. al., Inflammation: Basic Principles and Clinical Correlates, 2d Ed. Chapter 40, pp 821–839 (1992). In fact, cells made genetically deficient in HSPG's require exogenous heparin for growth.

Heparin is commonly administered in doses of up to 400 U/kg during surgical procedures such as cardiopulmonary bypass, cardiac catherization and hemodialysis procedures in order to prevent blood coagulation during such procedures. The anticoagulant effect of heparin in blood is a result of the interaction of heparin with ATIII. The heparin/ATIII complex is a potent inhibitor of many of the clotting factors of the coagulation cascade. Specific inhibition has been demonstrated for activated Factors IXa, Xa, XIa, XIIa and thrombin. The heparin/ATIII complex has the highest affinity for Factor Xa and thrombin which are common to both the intrinsic and extrinsic clotting pathways involved as the last two steps of the clotting cascade that results in the conversion of fibrinogen to fibrin.

When heparin is administered for anticoagulant effects during surgery, it is an important aspect of post-surgical therapy that the effects of heparin are promptly neutralized so that normal coagulation function can be restored. Currently protamine is used to neutralize heparin. Protamines are simple proteins of low molecular weight which are commonly isolated from salmon sperm. They are rich in arginine amino acid residues and strongly basic. Administered alone, protamines (usually in the form of protamine sulfate) have anti-coagulant effects. When administered in the presence of heparin, a stable complex is formed and the anticoagulant activity of both drugs is lost. Significant hypotensive and anaphylactoid effects of protamine have limited its clinical utility.

Other reported compounds which have heparin binding activity include platelet factor 4 (PF4) and major basic protein, see U.S. Pat. No. 5,086,164. Major basic protein demonstrates heparin binding activity but is also highly toxic.

Angiogenesis

Angiogenesis is closely associated with endothelial cell proliferation and constitutes the development of new capillary blood vessels. As such, it is an important process in mammalian development and growth, and in menstruation processes. The release of angiogenic growth factors, such as fibroblast growth factors 1–5, induces proliferation of endothelial cells via a heparin-dependent receptor binding mechanism. See Yayon et al., Cell, 64: 841–848 (1991). These heparin-binding growth factors can be released due to vascular trauma (wound healing), immune stimuli (autoimmune disease), inflammatory mediators (prostglandins) and from tumor cells.

Angiogenesis is also associated with a number of pathological conditions in which it would be desirable to inhibit such new blood vessel development. As one example, angiogenesis is critical to the growth, proliferation, and metastasis of various tumors. Other pathological conditions associated with angiogenesis include diabetic retinopathy, retrolental fibroplasia, neovascular glaucoma, psoriasis, angiofibromas, immune and non-immune inflammation including rheumnatoid arthritis capillary proliferation within atherosclerotic plaques, hemangiomas, endometriosis and Kaposi's Sarcoma.

Folkman et al., supra, discloses that psoriatic lesions in the skin are dominated by epithelial proliferation, neovascularization, and an infiltrate of inflammatory cells. It is unclear, however, whether angiogenesis is a step in the pathogenesis of psoriasis or a secondary phenomenon.

Several substances are known to function as angiogenesis inhibitors and have been reported to inhibit tumor angiogenesis, to prevent the onset of arthritis and to inhibit established arthritis in collagen-induced arthritis models, Peacock et al., J. Exp. Med., 175, 1135–1138 (1992). As one example, protamine is known to inhibit tumor angiogenesis and subsequent tumor growth. According to Taylor et al., Nature, 297: 307–312 (1982) protamine's anti-angiogenic activity is attributed to its ability to bind heparin. PF4 is also known to exhibit anti-angiogenic activity. Of interest to the present application is U.S. Pat. No. 5,112,946 which discloses modified PF4 and analogs thereof which have anti-angiogenic activity but lack the ability to bind heparin. PF4 has been shown to have at least two functional properties. Heparin binding has been studied most extensively, however, PF4 was originally described to have collagenase inhibitory properties. Collagenase inhibitors were the first inhibitors of angiogenesis to be discovered in 1973. See Folkman, supra. The mutations in the heparin binding region of PF4 were not examined for their effect on collagenase inhibitory activity. Interestingly, thrombospondin is also an inhibitor of angiogenesis and binds to heparin with a serine/tryptophan motif instead of a basic amino acid motif. Thus, there is no obvious prerequisite for heparin binding or for angiogenesis inhibition.

Published PCT patent application WO 92/01003 discloses the use of glycosaminoglycan (heparin) derivatives and their use as inhibitors of tumor invasiveness. Heparin derivatives are disclosed which are described as being substantially devoid of anticoagulation activity and which impede the formation of tumor metastases in a host.

Chronic Inflammation

Chronic inflammation is usually supported by angiogenesis. Arthritis is a chronic syndrome characterized by the inflammation of the peripheral joints accompanied by synovial thickening and the influx of immune factors and cells such as polymorphonuclear leukocytes (PMN). In rheumatoid arthritis, the inflammation is immune driven while in reactive arthritis, inflammation is associated with infection of the synovial tissue with pyogenic bacteria or other infectious agents. Folkman et al., supra, also note that many types of arthritis progress from a stage dominated by an inflammatory infiltrate in the joint to a later stage in which a neovascular pannus invades the joint and begins to destroy cartilage. While it is unclear whether angiogenesis in arthritis is a causative component of the disease, and not an epiphenomenon, there is evidence that angiogenesis is necessary for the maintenance of synovitis in rheumatoid arthritis. While nonsteroidal anti-inflammatory drugs (NSAIDs), corticosteroids and other therapies have provided improvements in relief for treatment of arthritis, there remains a need in the art for more effective therapies for arthritis and other inflammatory diseases.

Inflammation and angiogenesis are now understood to be separable but not mutually exclusive processes. Specific angiogenic proteins have been discovered that stimulate angiogenesis without inflammation and angiostatic steroids can inhibit angiogenesis without decreasing acute inflammation. See Folkman, supra. Interestingly, endotoxin has been identified as the most potent exogenous stimulator of angiogenesis through its stimulation of macrophage cytokines and growth factors.

Bacteicidal/Permeability-Increasing Protein

Bactericidal/permeability-increasing protein (BPI) is a protein isolated from the granules of mammalian PMNs, which are blood cells essential in the defense against invading microorganisms. Human BPI protein that has been isolated from polymorphonuclear neutrophils by acid extraction combined with either ion exchange chromatography [Elsbach, J. Biol. Chem., 254: 11000 (1979)] or $E.$ $coli$ affinity chromatography [Weiss, et al., Blood, 69: 652 (1987)] is referred to herein as natural BPI and has potent bactericidal activity against a broad spectrum of gram-negative bacteria. The molecular weight of human BPI is approximately 55,000 daltons (55 kD). The amino acid sequence of the entire human BPI protein, as well as the DNA encoding the protein, have been elucidated in FIG. 1 of Gray et al., J. Biol. Chem., 264: 9505 (1989), incorporated herein by reference.

The bactericidal effect of BPI has been shown to be highly specific to sensitive gram-negative species, while non-toxic for other microorganisms and for eukaryotic cells. The precise mechanism by which BPI kills bacteria is as yet unknown, but it is known that BPI must first attach to the surface of susceptible gram-negative bacteria. This initial binding of BPI to the bacteria involves electrostatic interactions between the basic BPI protein and the negatively charged sites on lipopolysaccharides (LPS). LPS has been referred to as "endotoxin" because of the potent inflammatory response that it stimulates. LPS induces the release of mediators by host inflammatory cells which may ultimately result in irreversible endotoxic shock. BPI binds to Lipid A, the most toxic and most biologically active component of LPS.

In susceptible bacteria, BPI binding is thought to disrupt LPS structure, leading to activation of bacterial enzymes that degrade phospholipids and peptidoglycans, altering tile permeability of the cell's outer membrane, and ultimately causing cell death by an as yet unknown mechanism. BPI is also capable of neutralizing the endotoxic properties of LPS to which it binds. Because of its gram negative bactericidal properties and its ability to neutralize LPS, BPI can be utilized for tile treatment of mammals suffering from diseases caused by Gram-negative bacteria, such as bacteremia or sepsis.

A proteolytic fragment corresponding to the N-terminal portion of human BPI holoprotein possesses the antibacterial efficacy of the naturally-derived 55 kD human holoprotein. In contrast to the N-terminal portion, the C-terminal region of the isolated human BPI protein displays only slightly detectable anti-bacterial activity. Ooi, et al., J. Exp. Med., 174: 649 (1991). A BPI N-terminal fragment, comprising approximately the first 199 amino acid residues of the human BPI holoprotein and referred to as "rBPI$_{23}$", has been produced by recombinant means as a 23 kD protein. Gazzano-Santoro et al., Infect. Immun. 60: 4754–4761 (1992).

Of interest to the present application are the disclosures in PCT International Application PCT/US91/05758 having publication No. WO 92/03535 relating to compositions comprising a BPI protein and an anionic compound which compositions are said to exhibit (1) no bactericidal activity and (2) endotoxin neutralizing activity. Anionic compounds are preferably a protein such as serum albumin but can also be a proteoglycan such as heparin. In addition, Weiss et al., J. Clin. Invest., 55: 33–42 (1975) discloses that heparin sulfate and LPS bind to block expression of the permeabiilty increasing activity of BPI. Neither reference discloses neutralization of heparin by combination with BPI, however.

There continues to exist a need in the art for new products and methods for use in neutralization of heparin, inhibition of tumor and angiogenesis, endothelial cell proliferation and treatment of chronic inflammation.

SUMMARY OF THE INVENTION

According to one aspect of the invention, methods are provided for neutralizing the anti-coagulant activity of heparin comprising administering an effective amount of a BPI protein product in vivo to a subject or in vitro to a fluid sample containing heparin.

According to another aspect of the invention, a BPI protein product is administered to subjects in order to inhibit endothelial cell proliferation including but not limited to endothelial cell proliferation associated with anglogenesis. The invention provides methods of inhibiting angiogenesis associated with a variety of clinical conditions. Specifically provided by the invention are methods of treating cancer by inhibiting angiogenesis associated with malignant tumor proliferation; Kaposi's sarcoma lesions and the like. Cancers susceptible to treatment by administration of BPI protein products include melanoma, sarcomas, and carcinomas including but not limited to breast, colon, lung, and prostate carcinomas. Other conditions for which BPI protein products can be administered for inhibition of angiogenesis include ocular retinopathy, retrolental fibroplasia, psoriasis, angiofibromas, endometriosis, hemangiomas and the like. Also contemplated by the invention are methods of contraception comprising administration of an effective amount of a BPI protein product to the uterine lining so as to prevent implantation of a fertilized ovum.

The invention also provides methods of treating chronic inflammatory disease states such as arthritis, psoriasis, inflammatory bowel disease, Crohn's disease, ulcerative colitis, lupus erythematosus, autoimmune uveitis, Lyme disease, and asthma comprising administering an effective amount of a BPI protein product to a subject suffering from the inflammatory disease state.

The invention also provides methods of preparation of medicaments for neutralization of the anti-coagulant properties of heparin, inhibition of tumor and endothelial cell proliferation, inhibition of angiogenesis and treatment of chronic inflammatory disease states.

Such medicaments can be prepared for oral administration or by injection or other parenteral methods and preferably include conventional pharmaceutically acceptable carriers and adjuvants as would be known to those of skill in the art. The medicaments are preferably in the form of a unit dose in solid, semi-solid and liquid dosage forms such as tablets, pills, powders, liquid solutions or suspensions, and injectable and infusible solutions. Effective dosage ranges from about 100 $\mu$g/kg to about 10 mg/kg of body weight are contemplated.

As used herein, "BPI protein product" includes naturally and recombinantly produced bactericidal/permeability-increasing protein, natural synthetic, and recombinant biologically active polypeptide fragments of bactericidal/permeability increasing protein, and biologically active polypeptide analogs, including hybrid fusion proteins, of either bactericidal/permeability increasing protein or biologically active fragments thereof.

DETAILED DESCRIPTION

Figure 1:
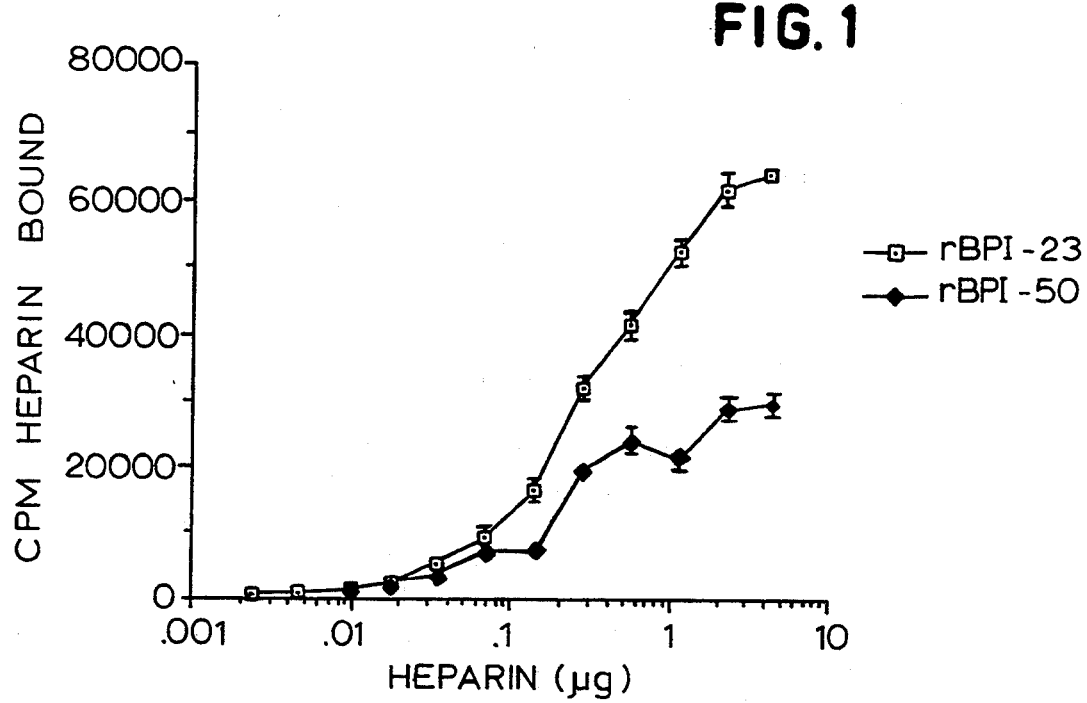
FIG. 1 depicts a graph of a heparin binding assay for rBPI$_{23}$ and rBPI$_{50}$.

The present invention relates to the administration of bactericidal/permeability-increasing protein (BPI) protein products for the treatment of a variety of therapeutic conditions not directly associated with bacterial infection.

While BPI is known as a potent cytotoxin for gram negative bacteria and is further known for neutralizing the adverse effects of lipopolysaccharide associated with the cell walls of grain negative bacteria, a variety of therapeutic effects for BPI protein products not directly associated with the gram negative bacterial infection have been discovered. Specifically, the invention provides methods for treating conditions not directly associated with gram negative infections including neutralization of the anti-coagulant activity of heparin, inhibition of tumor and endothelial cell proliferation including cell proliferation associated with angiogenesis and treatment of chronic inflammatory disease states such as arthritis.

The BPI protein products including biologically active fragments of BPI holoprotein which are to be administered according to the methods of this invention may be generated and/or isolated by any means known in the art. Co-owned, copending U.S. patent application Ser. No. 07/885,501, hereby incorporated by reference, discloses novel methods for the purification of recombinant BPI protein products expressed in and secreted from genetically transformed mammalian host cells in culture and discloses how one may produce large quantities of recombinant BPI products suitable for incorporation into stable, homogeneous pharmaceutical preparations.

Biologically active fragments of BPI include biologically active molecules that contains the same amino acid sequence as a BPI holoprotein, except that tile molecule lacks amino-terminal amino acids, internal amino acids, and/or carboxy-terminal amino acids of the holoprotein. By way of nonlimiting examples, such fragments include those described herein and the previously mentioned natural 25 kD fragment and a recombinant 23 kD, 199 amino acid residue amino-terminal fragment of the human BPI holoprotein referred to as rBPI$_{23}$. See, Gazzano-Santoro et al., Infect. Immun. 60: 4754–4761 (1992). In that publication, an expression vector was used as a source of DNA encoding a recombinant expression product (rBPI$_{23}$) having the 31-residue signal sequence and tile first 199 amino acids of the N-terminus of the mature human BPI, as set out in SEQ ID NOs: 1 and 2 taken from Gray et al., supra, except that valine at position 151 is specified by GTG rather than GTC and residue 185 is glutamic acid (specified by GAG) rather than lysine (specified by AAG). Recombinant holoprotein referred to herein as rBPI$_{50}$ has also been produced having the sequence set out in SEQ ID NOs: 1 and 2 taken from Gray et al., supra, with the exceptions noted for rBPI$_{23}$.

Biologically active analogs of BPI include but are not limited to recombinant hybrid fusion proteins comprising BPI holoprotein or biologically active fragment thereof, and at least a portion of at least one other polypeptide. Such proteins are described by Theofan et al. in co-owned, copending U.S. patent application Ser. No. 07/885,911, which is incorporated herein by reference in its entirety and include hybrid fusion proteins comprising, at the amino terminal end, a BPI protein or a biologically active fragment thereof and, at the carboxy terminal end, at least one constant domain of an immunoglobulin heavy chain or allelic variant thereof.

Biologically active analogs of BPI also include but are not limited to BPI protein products wherein one or more amino acid residue has been replaced by a different amino acid. For example, co-owned, copending U.S. patent application Ser. No. 08/013,801, filed Feb. 2, 1993, which is incorporated herein by reference, discloses polypeptide analogs of BPI and BPI fragments wherein a cysteine residue at position 132 or at position 135 is replaced by a different amino acid The administration of BPI protein products is preferably accomplished with a pharmaceutical composition comprising a BPI protein product and a pharmaceutically acceptable diluent, adjuvant, or carrier. The BPI protein product composition may be administered without or in conjunction with known antibiotics, surfactants, or other chemotherapeutic agents. A preferred pharmaceutical composition containing BPI protein products comprises BPI at a concentration of 1 mg/ml in citrate buffered saline (0.02 M citrate, 0.15 M NaCl, pH 5.0) comprising 0.1% by weight of poloxamer 188 (Pluronic F-68, BASF Wyandotte, Parsippany, NJ) and 0.002% by weight of polysorbate 80 (Tween 80, ICI Americas Inc., Wilmington, DE). Such preferred combinations are described in co-owned, copending, U.S. patent application Ser. No. 08/012, 360, filed Feb. 2, 1993, the disclosure of which is incorporated herein by reference.

Effective doses of BPI and BPI protein products for partial or complete neutralization of the anti-coagulant activity of heparin and other effects described herein may be readily determined by those of skill in the art according to conventional parameters including the size of the subject, the quantity of heparin administered to the subject and the time since administration of the heparin.

Other aspects and advantages of the present invention will be understood upon consideration of the following illustrative examples. Example 1 addresses assay systems for quantification of heparin binding by BPI protein products; Example 2 describes the relative capacity of heparin to block binding of bacterial LPS to BPI protein products: Examples 3 and 4, respectively, present results of tests for the capacity of BPI protein products to inhibit thrombin or Factor Xa inactivation by antithrombin III/heparin complexes; and Example 5 relates to the effect of BPI protein products on heparin-mediated lengthening of thrombin time. Examples 6-8 relate to administration of BPI protein products of in collagen and bacterial induced arthritis animal model systems exemplifying treatment of chronic inflammatory disease states. Examples 9-10 illustrate testing of BPI protein products for angiostatic effects in a mouse malignant melanoma metastasis model system. Example 11 addresses effects of BPI protein products on endothelial cell proliferation and possible binding mechanisms involved. Examples 12-14 illustrate heparin-binding, LPS-binding and bactericidal activities for BPI protein product synthetic peptides.

EXAMPLE 1

Heparin binding assays were conducted using membrane bound natural and recombinant BPI molecules and radiolabelled heparin. Briefly, rBPI$_{23}$ and holoprotein designated rBPI$_{50}$ were added to wells of a 96-well microtiter plate having an Imobilon-P (Millipore, Bedford, Mass.) membrane disposed at bottom of the wells. Five $\mu$g of protein was added to each well. The wells were dried and subsequently blocked with a 0.1% bovine serum albumin (BSA) in phosphate buffered saline, pH 7.4 (blocking buffer.) Dilutions of $^3$H-heparin (DuPont, NEN, Wilmington, Del.) were made in the blocking buffer and incubated in the rBPI$_{23}$ containing wells for one hour at 4° C. The unbound heparin is aspirated and the wells were washed three times with blocking buffer, dried and removed for quantitation in a liquid scintillation counter. Typical assay results are graphically presented in FIG. 1. While BSA in the blocking buffer does have a low affinity and capacity to bind heparin, this was considered physiologically irrelevant and the background was routinely subtracted from the test compound signal.

Similar assays compared heparin binding by rBPI$_{23}$, rBPI$_{50}$, and natural holoprotein (BPI$_{55}$) with thaumatin or with wash buffer (1% BSA) as controls. In these assays, relatively little heparin binding by the natural and rBPI$_{50}$ holoproteins was observed. The lesser extent of binding by rBPI$_{50}$ and nBPI$_{55}$ may have been the result of carbohydrate contamination of the protein preparations.

In addition, binding constants with $^3$H-heparin as the ligand were determined using nonlinear function minimization with Grafit software (Erithicus Softward Ltd., Staines, UK) for rBPI$_{23}$, rBPI$_{50}$, protamine and thaumatin with the results shown in Table 1 below.

TABLE 1

Binding Constants with $^3$H-heparin as the Ligand

| HEPARIN BINDING PROTEIN | $K_d$ | CO-OPERA-TIVITY | CAPACITY | HEPARIN COLUMN NaCl ELUTION |
|---|---|---|---|---|
| rBPI$_{23}$ | 79 nM | 1.93 | 2.63 $\mu$g | 0.84 M |
| rBPI$_{50}$ | 173 nM | 1.18 | 1.30 $\mu$g | 0.81 M |
| Protamine | 8.1 nM | 1.02 | 2.66 $\mu$g | 1.33 M |
| Thaumatin | | no binding | | 0.15 M |

EXAMPLE 2

The ability of heparin and of soluble Lipid A, LPS, and Teichoic acids to compete with immobilized E. coli J5 Lipid A for binding to soluble rBPI$_{23}$ were assessed. Specifically, Immulon 2 (Dynatech, Chintilly, Va.) microtiter wells were coated with E. coli J5 Lipid A at a concentration of 0.5 $\mu$g/mL in methanol (50 $\mu$L volume ). The wells were then blocked for 4 hours at 37° C. with PBS containing 0.1% BSA. Control wells were treated with 50$\mu$L of plain methanol and then blocked as above. The blocked wells were aspirated and washed twice with PBS/0.05% Tween-20. Varying concentrations of putative inhibitors were plated onto the wells in a volume of 25$\mu$L PBS, followed by 200,000 cpm of radio-iodinated rBPI$_{23}$ in 25$\mu$L of PBS containing 0.1% Tween-20. The test solutions included Ra LPS from

Figure 2:
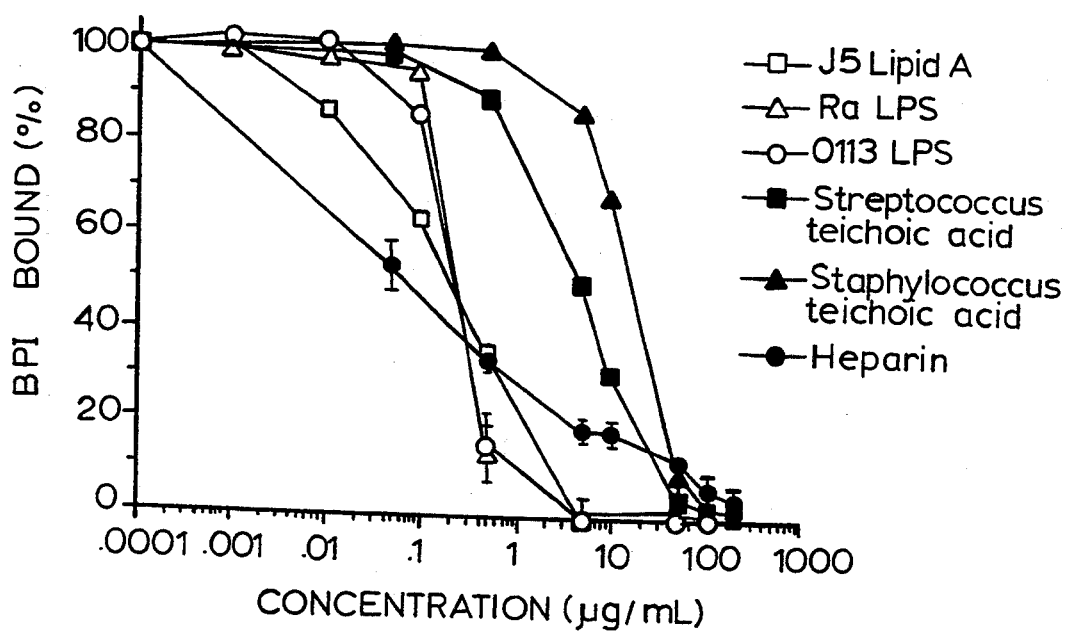
FIG. 2 depicts a graph showing the effect of heparin on rBPI binding to E. coli J5 Lipid A compared to various LPS and teichoic acid samples.

*Salmonella minnesota* R60 at 200µg/mL; Smooth LPS from *E. coli* 0113 (RIBI Immunochem, Hamilton, Mont., #R318) at 200µg/mL; Lipoteichoic acid from *Streptococcus faecalis*, (Sigma, St. Louis, Mo., #L-4015) at 400 µg/mL; Lipoteichoic acid from *Staphylococcus Aureus*, (Sigma #L-2525) at 400 µg/mL; and heparin sodium USP injection (Lypho-Med, Rosemont, Ill., #915501 ) at 400 µg/mL. Binding was allowed to proceed overnight at 4° C. with gentle shaking, after which the wells were aspirated, washed three times with PBS/0.05% Tween-20, and counted. The results as set out in FIG. 2 show a high affinity of $rBPI_{23}$ for heparin and also that heparin block a greater proportion of BPI binding to Lipid A at concentrations of up to 0.1µg/mL than any of the LPS or teichoic acid inhibitors.

EXAMPLE 3

A chromostrate assay was used to determine the effect of $rBPI_{23}$ on thrombin inactivation by ATIII/heparin complexes. Specifically, a Chromostrate anti-thrombin assay kit (Organon Teknika Corp., Durham, N.C.) was used to examine the inhibition of purified thrombin by preformed ATIII/heparin complexes in plasma.

Figure 3:
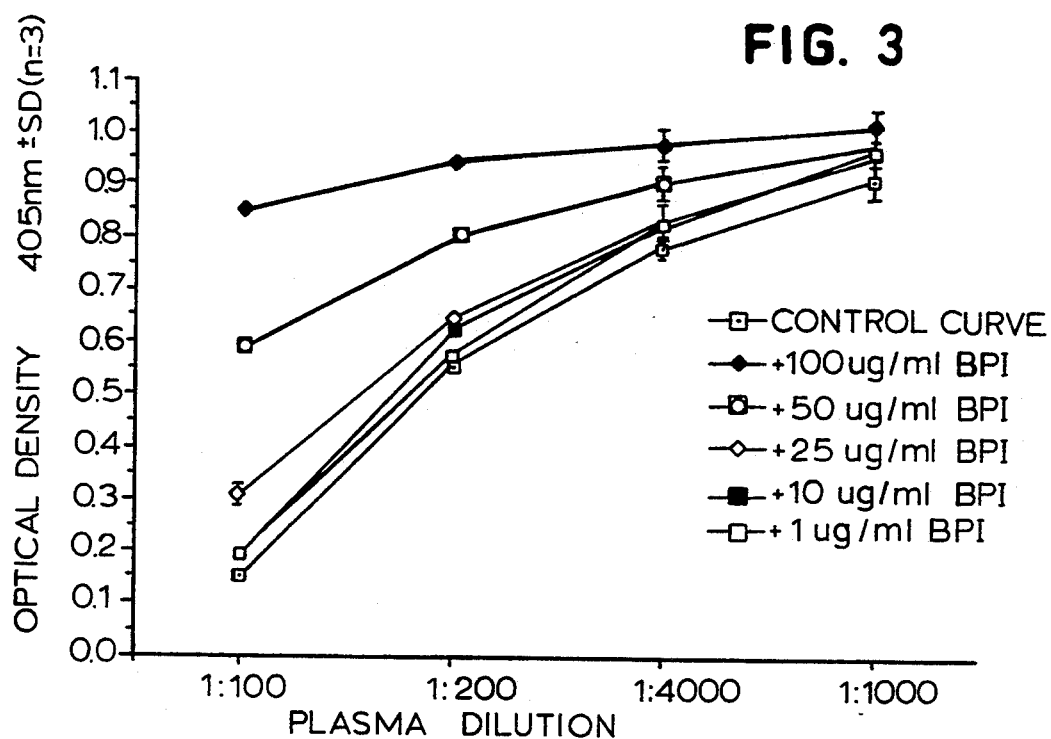
FIG. 3 depicts a graph showing the effect of rBPI$_{23}$ on ATIII/heparin inhibition of thrombin.

The assay was performed in 96 well microtiter plates with a final volume per well of 200 µg/mL. The order of addition of assay components was as follows: diluted heparinized reference plasma (50 µL); thrombin 1nKat/mL (50 µL ); 50 µL $rBPI_{23}$ or thaumatin (a control protein) at concentrations ranging from 1.0 µg/mL to 100 µg/mL; and thrombin chromogenic substrate 1 µmole/mL (50 µL). The reaction was allowed to proceed for 5 minutes and the color reaction was quantitated on a microplate reader. The assay results shown in FIG. 3 indicate that $rBPI_{23}$ can effectively neutralize ATIII/heparin complexes in heparinized human plasma in a dose dependent manner. As the plasma was titrated the amount of thrombin activity increased. This was caused by a decrease in the amount of inhibitory ATIII/heparin complexes in the added plasma. The control protein, thaumatin, was essentially equivalent in effect to the buffer control at all protein concentrations.

EXAMPLE 4

A chromostrate assay was used to determine the effect of $rBPI_{23}$ on Factor Xa neutralization by ATIII/heparin complexes. Specifically, the assay was conducted using a chromostrate heparin anti-Factor Xa assay kit (Organon Teknika Corp.) and was performed under fixed concentrations of Factor Xa and ATIII. Heparin concentration was varied so that a heparin standard curve was generated for determination of unknown heparin concentrations in clinical samples. The assay measured functional Factor Xa activity by the release of a chromogenic compound from a synthetic substrate. ATIII/heparin complexes neutralize Factor Xa activity, thus the amount of chromogen released was inversely related to the amount and anti-Factor Xa activity of heparin in the assay sample.

Figure 4:
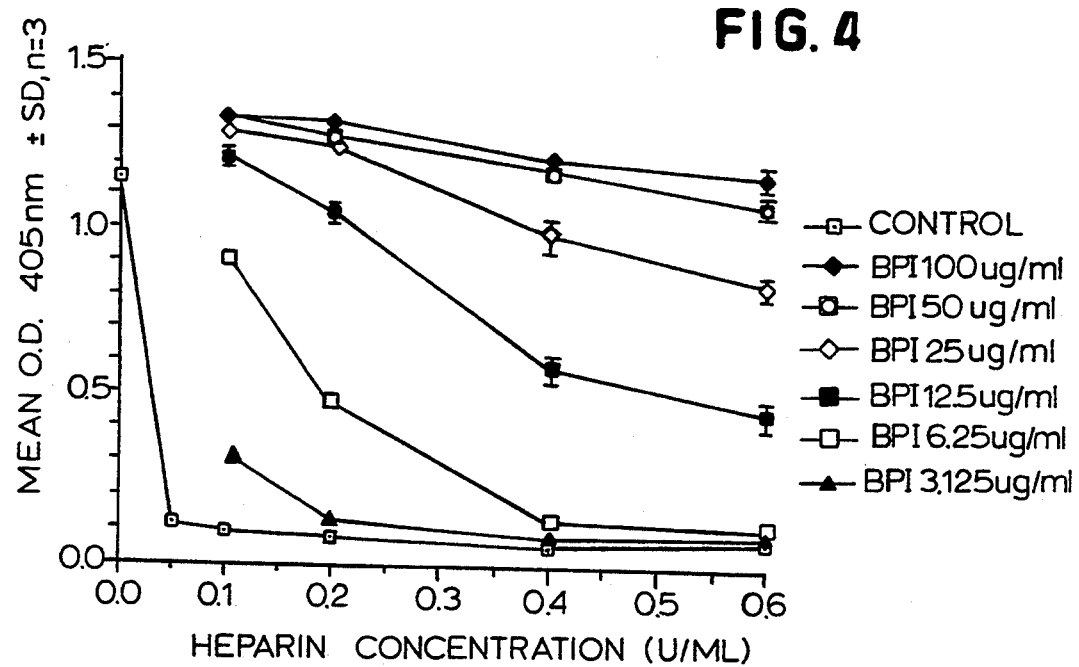
FIG. 4 depicts a graph showing the effect of rBPI$_{23}$ on ATIII/heparin inhibition of Factor Xa.

The assay was performed in 96 well microtiter plates with a final volume per well of 200 µL. Assay components were added to the microtiter wells as follows: 50 µL of purified Factor Xa (.14nKat/mL), 25 µL purified bovine ATIII (0.5 U/mL), 25 µL heparin (from 0.0 to 0.6 U/mL), 50 µL $rBPI_{23}$ or the control thaumatin at various concentrations (from 3.125 µg/mL to 100 µg/mL) and 50 µL substrate (3 µmoles/mL). The reaction was allowed to proceed for 5 minutes and then the color reaction was quantitated on a microplate reader. The assay results shown in FIG. 4 indicates that $rBPI_{23}$ can effectively neutralize heparin in the ATIII/heparin inhibition of Factor Xa. As the concentration of heparin is increased, the amount of $rBPI_{23}$ necessary for heparin neutralization also increased. The control protein, thaumatin, was essentially equivalent in effect to the buffer control at all protein concentrations.

EXAMPLE 5

Figure 5:
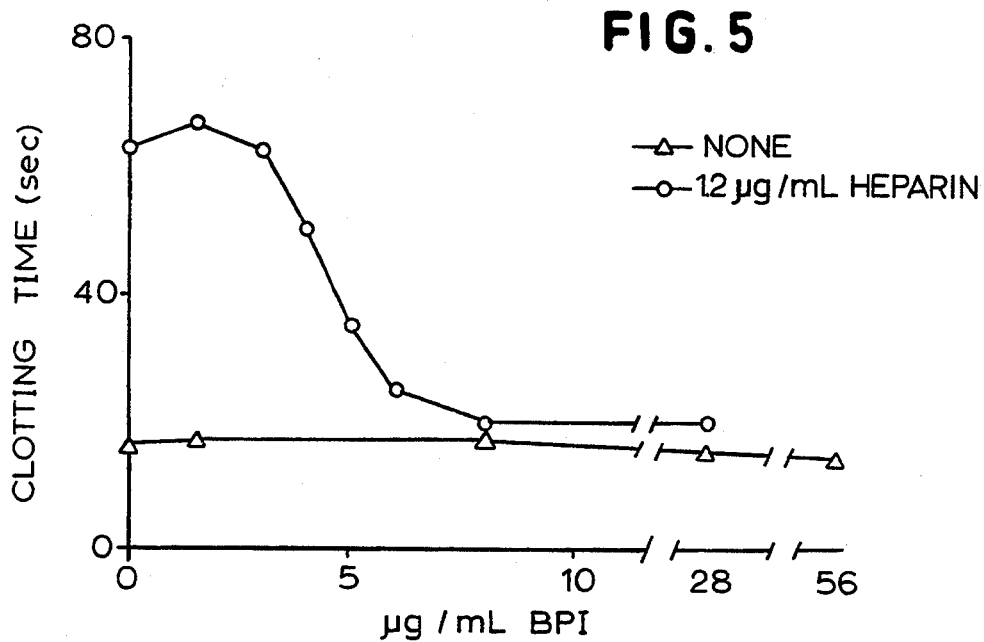
FIG. 5 depicts a graph showing the effect of rBPI$_{23}$ on heparin-mediated lengthening of thrombin time in human plasma.

The effect of $rBPI_{23}$ was determined on heparin-mediated lengthening of thrombin time, i.e., the time required for clotting of a mixture of thrombin and plasma. Thrombin time is lengthened by the presence of endogenous or exogenous inhibitors of thrombin formation, such as therapeutically administered heparin. Agents which neutralize the anticoagulant effects of heparin will reduce the thrombin time measured by the test. Human citrated plasma (200 µL) was incubated for 1 minute at 37° C. with either 15 µL of diluent (0.15 M NaCl, 0.1 M Tris, pH 7.4) or 15 µL of the diluent also containing 25 µg/mL heparin (187 units/mg). Various concentrations of $rBPI_{23}$ )from 0.0 to 56 µg/mL) in a volume of 15 µL were added, followed immediately by 100 µL of thrombin reagent (Sigma Chemical Co., No. 845-4). Clotting time (thrombin time) was measured using a BBL Fibrometer (Becton Dickenson Microbiology Systems, Cockeysville, Md.). The results shown in FIG. 5 establish that $rBPI_{23}$ inhibits the heparin-mediated lengthening of thrombin time. In the absence of heparin, $rBPI_{23}$ had no effect on the assay even at concentrations as high as 56 µg/mL.

The results of Examples 1 through 5 show that $rBPI_{23}$ binds to heparin in direct binding assays and effectively neutralizes heparin inhibition of coagulation proteases. Based on these characteristics, BPI protein products are projected to be useful in the clinical neutralization of heparin anti-coagulant effects in dosages generally corresponding functionally to those recommended for protamine sulfate, but are not expected to possess the severe hypotensive and anaphylactoid effects of that material.

A further aspect of the present invention relates to the discovery of the utility of BPI to treat and prevent the effects of chronic inflammatory disease states such as arthritis, including rheumatoid and reactive arthritis, psoriasis, inflammatory bowel disease, Crohn's disease, ulcerative colitis, lupus erythematosus, autoimmune uveitis, Lyme disease, and asthma. Exemplary methods are provided for treating subjects suffering from arthritis comprising administering an effective amount of a BPI protein product in order to prevent or treat arthritis. The BPI protein product may be administered topically, or by injection such as intraarticularly, intravenously, intramuscularly or subcutaneously or by other parenteral and non-parenteral methods.

EXAMPLE 6

The effect of administration of BPI protein products was studied in a collagen-induced arthritis model. Specifically, arthritis was induced in mice by intradermal immunization of bovine Type II collagen at the base of the tail according to the method of Stuart et al., *J. Clin. Invest.*, 69: 673-683 (1982). Generally, mice begin to develop arthritic symptoms at Day 21 after collagen immunization. The arthritic scores of the treated mice were then evaluated in a blinded fashion over a period of 120 days for mice treated on each of days 21-25 with doses of either $rBPI_{23}$, thaumatin control protein, or buffer which were injected intravenously via the tail vein.

Specifically, bovine Type II collagen (Southern Biotechnology Associates, Inc., Birmingham Ala.) was administered via intradermal injection (0.1 mg/mouse) at the base of the tail on day 0 to groups of ten male mice (Mouse/DBA/1J), each weighing approximately 20–25 g grams. $rBPI_{23}$ was dissolved in 0.5 M NaCl, 20 mM sodium acetate, pH 6.0 and diluted with PBS buffer (1 mg/ml) for administration at 0.125 mg/mouse. Thaumatin protein in PBS (0.121 mg/mouse), and PBS buffer alone (0.1 ml) were administered as controls.

Figure 6:
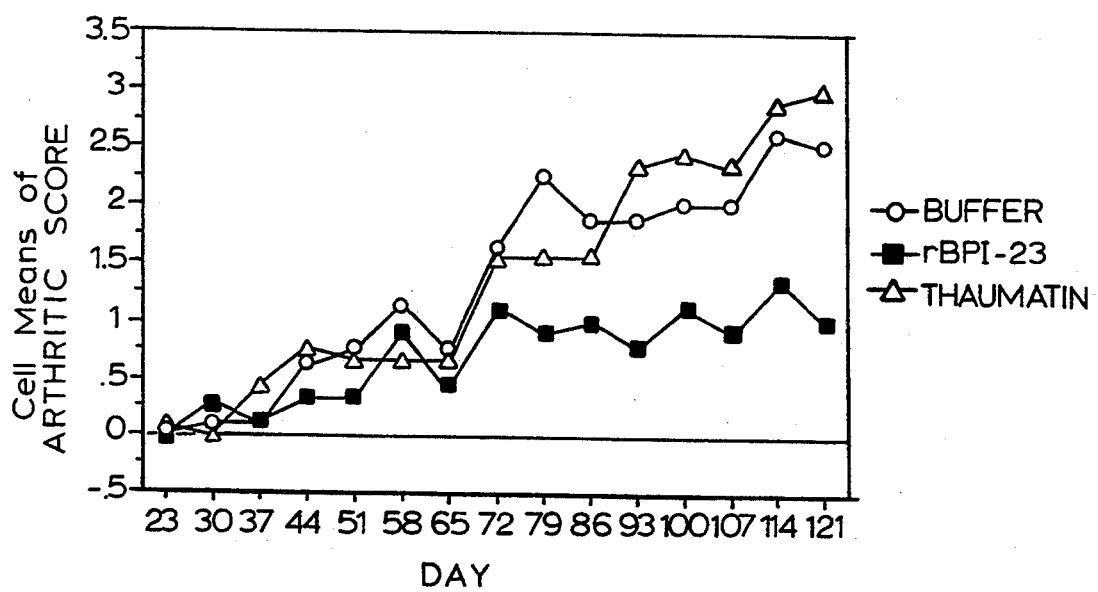
FIG. 6 depicts a graph showing the effect of rBPI$_{23}$ and thaumatin control protein on arthritic scores in a collagen-induced arthritis model with mild arthritis.

The results shown in FIG. 6 show that the BPI has a statistically significant effect in reducing the arthritic score of treated mice compared with the PBS buffer and thaumatin protein controls.

EXAMPLE 7

Figure 7:
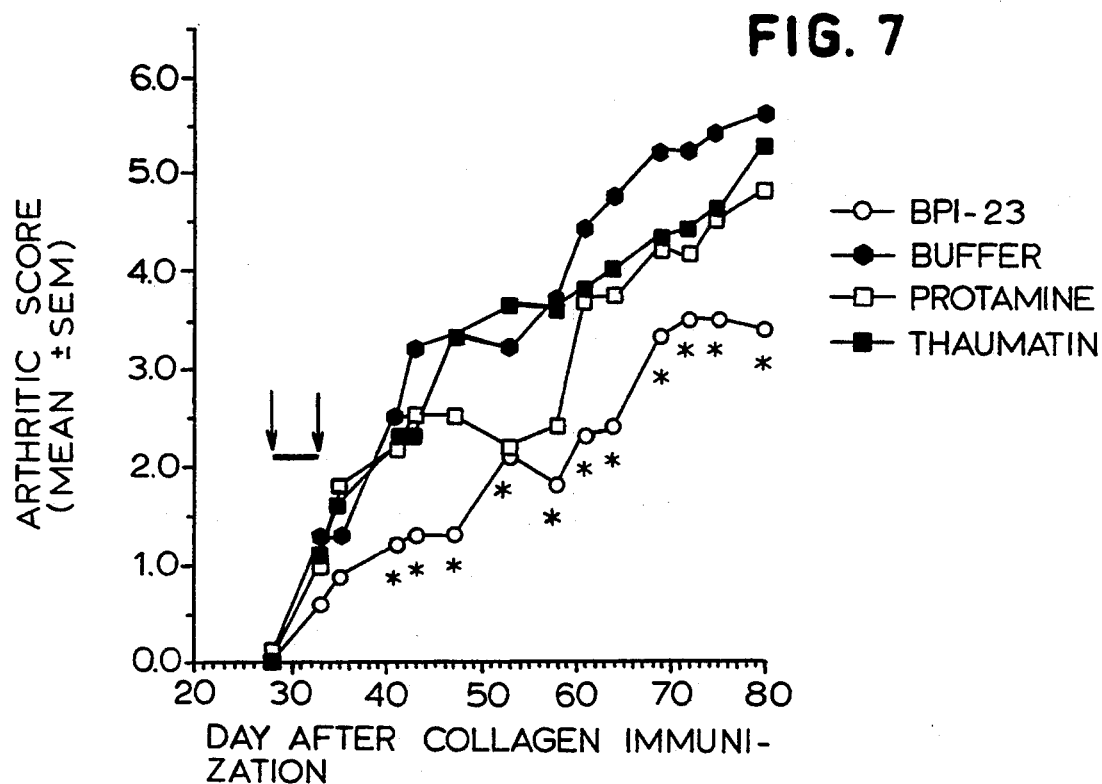
FIG. 7 depicts a graph showing the effect of rBPI$_{23}$ and protamine on arthritic scores in a collagen-induced arthritis model with severe arthritis.

The collagen-induced arthritis model of Example 6 was used to evaluate the performance of a BPI protein product in comparison with protamine sulfate, and both thaumatin protein and buffer as controls. Specifically, $rBPI_{23}$ was dissolved in 0.5 M NaCl, 20 mM sodium acetate, pH 6.0 and diluted with PBS buffer (1 mg/ml) and was administered at 0.125 mg/mouse. The other test materials were administered at the following dosages: protamine sulfate (Sigma Chemical Co) (0.13 mg/mouse), thaumatin (0.121 mg/mouse), and PBS buffer (0.1 ml). Each of four groups of ten mice received test or control materials through intravenous injection via the tail vein on each of days 28 through 32. FIG. 7 discloses the results of arthritic scores for the various treatment and control protocols evaluated at days 28–80. The stars (*) in FIG. 7 represent a statistically significant difference between $rBPI_{23}$ and buffer at $p<0.01$ while the pluses (+) represent a statistically significant difference between $rBPI_{23}$ and buffer at $p<0.05$. These results show that the $rBPI_{23}$ significantly reduced arthritic score for mice treated in the model system.

EXAMPLE 8

In this example BPI protein products are administered to treat reactive arthritis in a *Yersinia enterocolitica* reactive arthritis model according to the method of Yong et al., *Microbial Pathogenesis*, 4: 305–310 (1988). Specifically, BPI protein products are administered to DBA/2J mice which have previously been injected intravenously with *Yersinia enterocolitica* WA at a dosage calculated to induce a non-septic arthritis in the mice.

The invention also provides methods for inhibiting endothelial cell proliferation and angiogenesis by administration of BPI protein products. Examples are specifically provided which address treatment of tumors in a mouse melanoma model system.

EXAMPLE 9

According to this example, a BPI protein product, protamine, and both thaumatin protein and buffer controls were tested for efficacy in a mouse malignant melanoma metastasis model. Specifically, four groups of nine C57BL/6J mice were inoculated with $10^5$ B16.F10 malignant melanoma cells via intravenous injection into the tail vein on day 0. Either $rBPI_{23}$ (0.13 mg/mouse), protamine sulfate (0.13 mg/mouse), thaumatin (0.13 mg/mouse) or PBS buffer (0.1 ml/mouse) were intravenously administered into the tail vein of the mice on days 1, 3, 6, 8, 10, 13, 15, 17, and 19. The animals were sacrificed via cervical dislocation on Day 20 for observation of lung tissues. The lobes of each lung were perfused and inflated by injecting 3 ml water into the lung via the trachea. Superficial tumor nodules were then counted with the aid of a dissecting microscope and the number of tumors found per group analyzed for statistically significant differences. While the data was not statistically significant, animals treated with $BPI_{23}$ had the lowest tumor load, followed by those treated with protamine, the thaumatin protein control and the buffer control. The lack of statistical significance (tumor number did not adequately reflect tumor size) indicated that a more specific assay methodology would be needed to determine the tumor load.

EXAMPLE 10

A BPI protein product, protamine, and both thaumatin protein and buffer controls were again tested for efficacy in the mouse malignant melanoma metastasis model of Example 9. Specifically, six groups of C57BL/6J mice were inoculated with $10^5$ B16. F10 malignant melanoma cells via intravenous injection into the tail vein on day 0. Either $rBPI_{23}$ (0.125 mg/mouse), protamine sulfate (0.125 mg/mouse), thaumatin (0.125 mg/mouse) or PBS buffer as set out in Table 2 below were intravenously administered into the tail vein of the mice on days 1, 2, 5, 7, 9, 12, 14, 16, and 19. All animals in groups A-D were sacrificed by cervical dislocation on day 20 for observation of lung tissues. The lungs were removed and placed into a beaker of cold water. The lobes of each lung were then perfused and inflated by injecting 3 ml of water into the lung via the trachea. Superficial tumor nodules are then analyzed for melanin content.

TABLE 2

| Group | Control/Test Article | No. of Animals |
|---|---|---|
| A | Buffer | 10 |
| B | Protamine | 10 |
| C | Thaumatin | 10 |
| D | $rBPI_{23}$ | 10 |
| E | Buffer | 5 |
| F | $rBPI_{23}$ | 5 |

Figure 8:
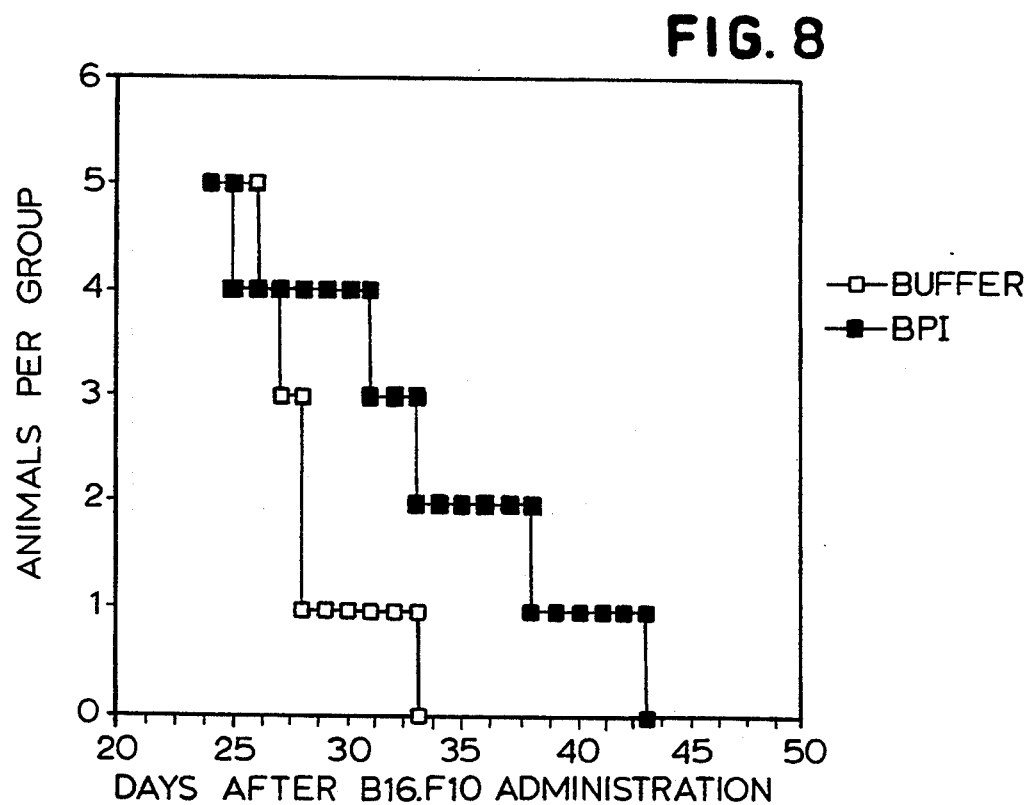
FIG. 8 depicts a graph showing survival of mice treated with BPI or a buffer in a mouse melanoma metastasis model.

Groups E and F comprising animals treated with either buffer or $rBPI_{23}$ respectively were not sacrificed but were observed once daily for mortality. FIG. 8 shows the survival data for the two groups of animals. Although all ten of the animals had died by day 43, the BPI treated mice generally survived significantly longer than the untreated mice indicating that BPI had an anti-angiogenic effect and slowed metastasis of the melanoma tumors.

According to an additional aspect of the invention, BPI protein products may be used to inhibit Kaposi's Sarcoma in a model system such as that of Miles et al., VII International Conference on AIDS, Florence, Italy, Paper 41(8), 1991.

EXAMPLE 11

Murine cerebral capillary endothelial cells (EC) as described in Bauer, *Microvascular Research* 37: 148–161 (1989) were passaged in Medium 199 containing Earle's salts, L-glutamine and 2.2 g/l of sodium bicarbonate (Gibco, Grand Island, N.Y., #400-100EB), plus 10% heat inactivated fetal calf serum (Irvine Scientific, Irvine, Calif.) and 1% penicillin/streptomycin (Gibco, #600-5140AG). Harvesting of the confluent cells was performed by trypsinization with trypsin-EDTA (Gibco #610-5300PG) for 3 minutes. The trypsinization was stopped by adding 10 ml of the passage medium to the flask. Proliferation assays were performed on freshly harvested EC in standard flat bottom 96 well microtiter plates. A final volume of 200 μl/well was maintained for each well of the assay. A total of $4 \times 10^4$ EC were added to each well with varying concentrations of rBPI$_{23}$, thaumatin control protein or buffer control. After 48 hours of culture in a 5% $CO_2$ incubator, 1 μCi of [methyl-$^3$H] thymidine in 10 μl of Medium 199 was added to each well. After a 24 hour pulse, the EC cells were harvested by trypsinization onto glass microfiber filters and incorporated [$^3$H]thymidine was quantitated with a gas proportional solid phase beta counter.

Figure 9:
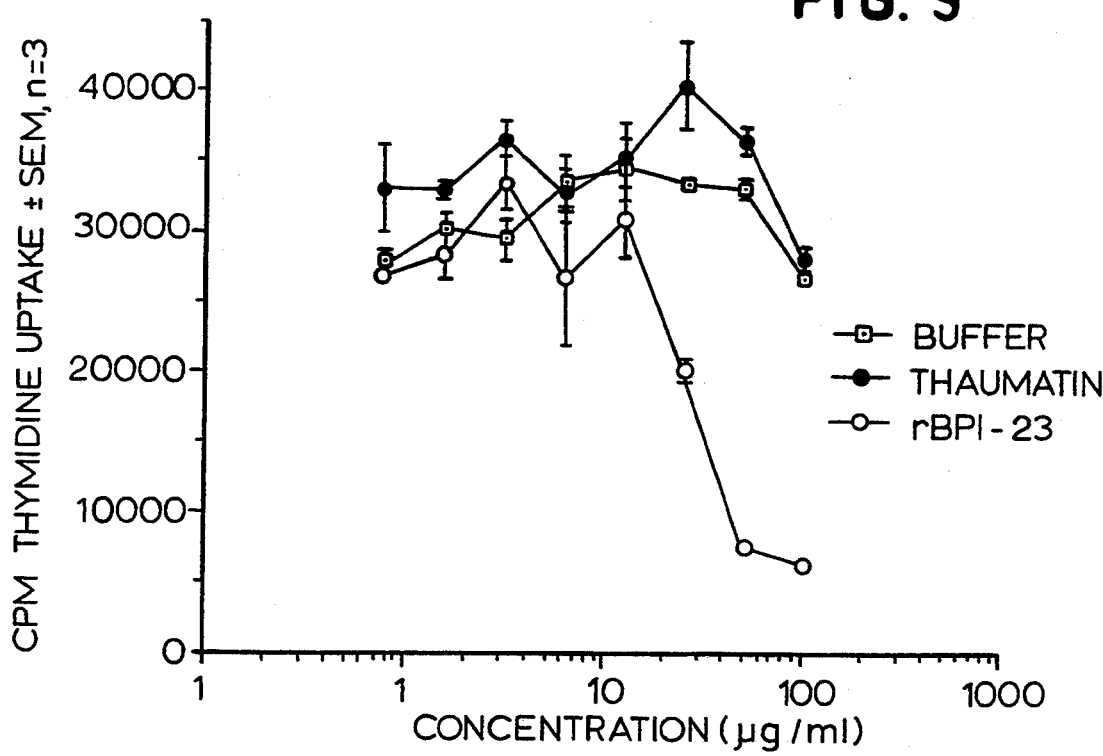
FIG. 9 depicts a graph showing the effect of rBPI$_{23}$ on Type II murine capillary endothelial cell proliferation.

Concentration dependent inhibition of EC cell proliferation by rBPI$_{23}$ is shown in FIG. 9. No effect was observed when similar concentrations of thaumatin or equal volumes of the buffer were added to the wells. The first inhibition of proliferation is observed at 12.4 μg/ml rBPI$_{23}$ and the effect appears to be maximal at 50 μg/ml. The growth of the EC cells is known to be dependent on FGF-2 (bFGF) in the calf serum and FGF-2 requires cell surface heparan for receptor activation (Yayon et al., Cell 64: 841–848, 1991). Without intending to be bound by a theory of the invention, it is believed that rBPI$_{23}$ bound to cell surface heparan on the EC cells interferes with the activation of the cells by FGF-2.

Direct binding studies of rBPI$_{23}$ on the EC cells were performed by harvesting the 10x passaged cells from a confluent flask and resuspending the trypsinized cells in 12.5 ml of culture medium. 0.5 ml of the suspension was added to each well of a standard 24 well tissue culture plate and incubated overnight. The plate was washed with 0.1% bovine serum albumin in phosphate buffered saline containing calcium and magnesium. (Gibco.) After washing, 0.5 ml of the BSA/PBS was added per well. Preliminary experiments indicated that 50 ng/ml of $^{125}$I-labeled rBPI$_{23}$ added to the wells produced approximately 30,000 specific cpm after a 3 hour, 4° C. incubation with 3x washing in PBS and lysis with 1 M NaOH from gamma counting of the lysate.

Figure 10:
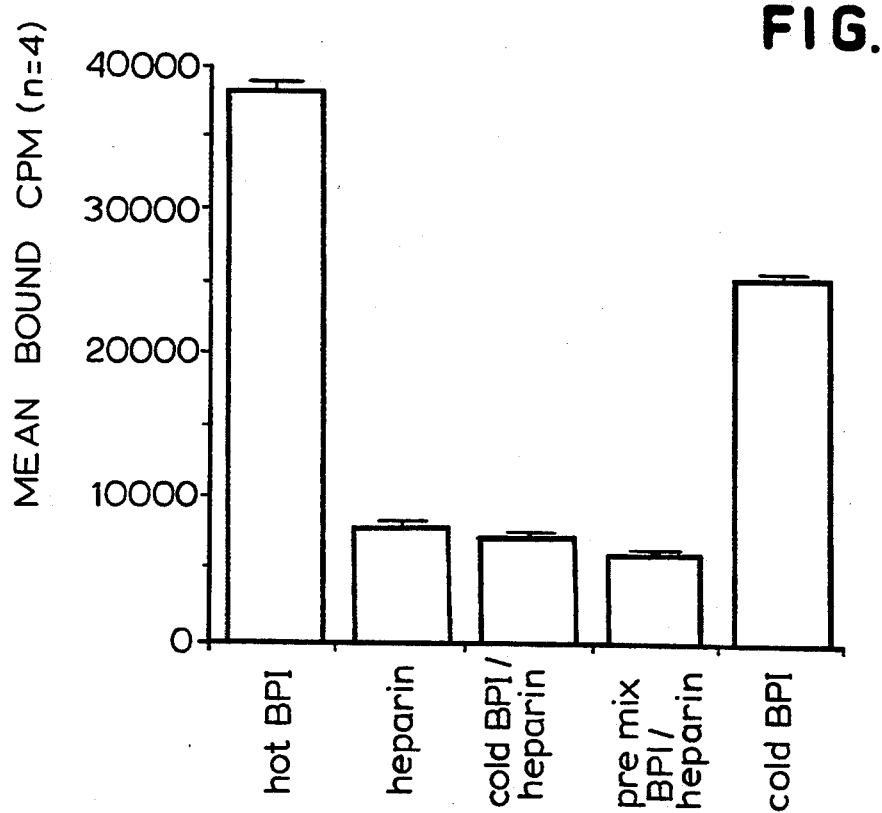
FIG. 10 illustrates BPI binding to epithelial cells.

The specific binding of 50 ng/ml $^{125}$I-labeled, "hot" rBPI$_{23}$ to the EC cells could be competed by addition of 20 μg/ml heparin (Sigma, Grade I). Similar competition was observed for unlabeled ("cold") rBPI$_{23}$ added to the binding culture. The combination of unlabeled rBPI$_{23}$ with heparin (concurrently added or pre-mixed prior to addition) could not reduce the binding below the heparin only competition (FIG. 10). These data indicate that rBPI$_{23}$ binds to endothelial cells via heparin-like molecule and that this binding appears to interfere with EC cell proliferation to a heparin binding growth factor (FGF-2).

In order to assess biological properties of peptide fragment BPI protein products, 15-mer amino acid synthetic peptides based on the 23 kD amino terminal fragment of BPI were prepared and evaluated for heparin-binding activity, activity in a Limulus Amoebocyte Lysate Inhibition (LAL) assay and bactericidal activity. Specifically, 47 synthetic peptides each comprising 15 amino acids and overlapping the adjacent peptides by 11 amino acids were prepared, in duplicate, based on the sequence of rBPI$_{23}$ described above.

Peptides were simultaneously synthesized according to the methods of Maeji et al., Immunol. Methods, 134: 23–33 (1990) and Gammon et al., J. Exp. Med., 173: 609–617 (1991), utilizing the solid-phase technology of Cambridge Research Biochemicals Ltd. under license of Coselco Mimotopes Pty Ltd. Briefly, the sequence of rBPI$_{23}$ (1–199) was divided into 47 different 15-mer peptides that progressed along the linear sequence of rBPI$_{23}$ by initiating a subsequent peptide every fifth amino acid. This peptide synthesis technology allows for the simultaneous small scale synthesis of multiple peptides on separate pins in a 96-well plate format. Thus, 94 individual pins were utilized for this synthesis and tile remaining to pins (B,B) were subjected to the same steps as the other pins without tile addition of activated FMOC-amino acids. Final cleavage of the 15-mer peptides from the solid-phase pin support employed an aqueous basic buffer (sodium carbonate, pH 8.3). The unique linkage to the pin undergoes a quantitative diketopiperazine cyclization under these conditions resulting in a cleaved peptide with a cyclo(lysylprolyl) moiety on the carboxyl-terminus of each peptide. The amino-termini were not acetylated so that the free amino group could potentially contribute to anion binding reactions. An average of about 15 μg of each 15-mer peptide is recovered per well.

EXAMPLE 12

Figure 11:
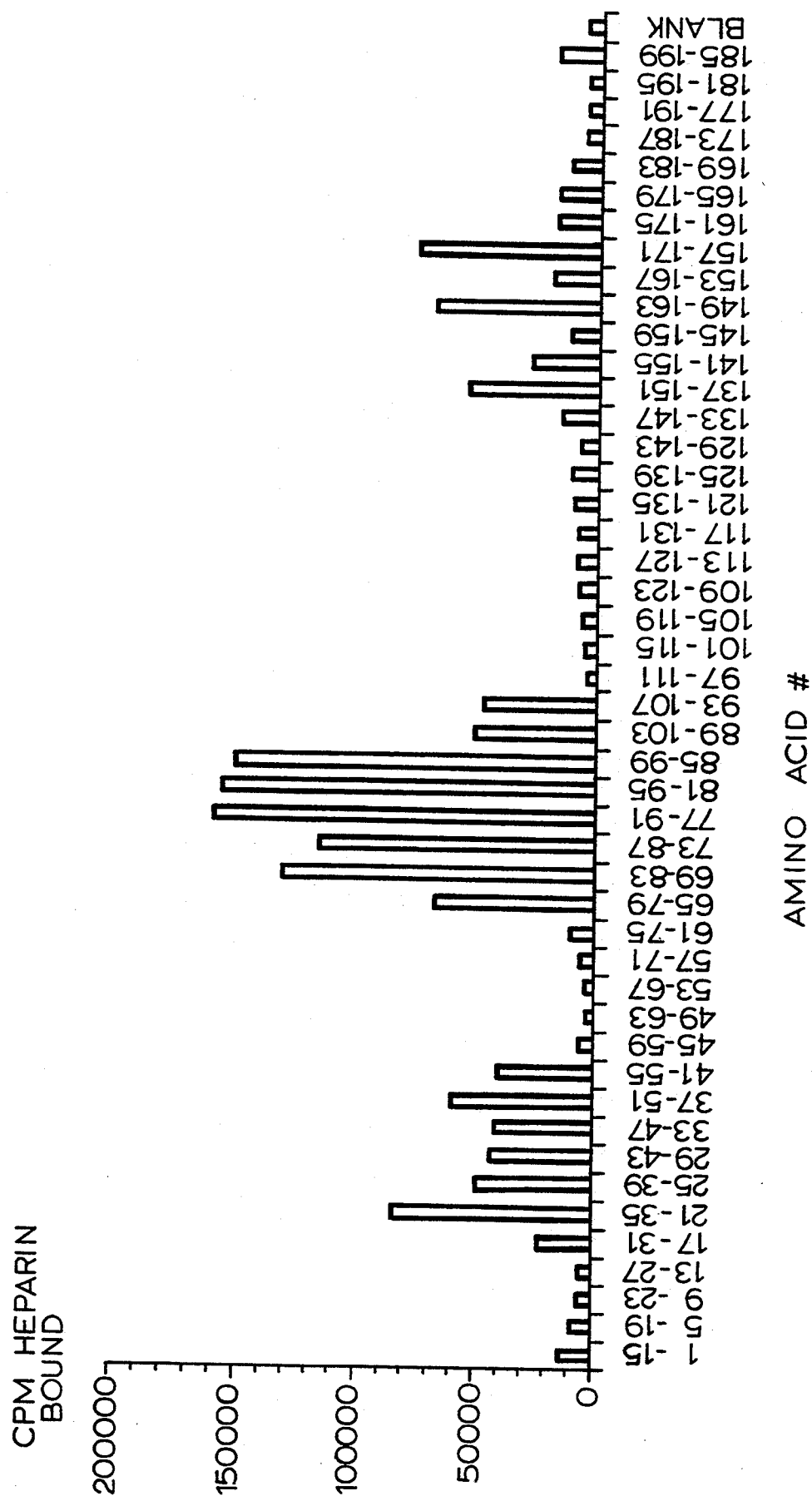
FIG. 11 depicts a graph of a heparin binding assay for synthetic BPI peptides.

The synthetic BPI protein product peptides described above were subjected to a heparin binding assay according to the methods described in Example 1. The results, as shown in FIG. 11, indicate the existence of three separate functional domains with heparin binding activity; the first extending from about amino acids 21–55; the second extending from about amino acids 65–107; and the third extending from about amino acids 137–171. Material from blank control pins had no heparin binding effects.

EXAMPLE 12

The synthetic BPI protein product peptides described above were Limulus Amoebocyte Lysate (LAL) inhibition assay to determine LPS binding properties. Specifically, the synthetic BPI peptides were mixed in Eppendorf tubes with a fixed concentration of E. coli 0113 LPS (4 ng/ml final) and incubated at 37° C. for 3 hours with occasional shaking. Addition controls comprising 0.05 μg/mL were also tested. Following incubation, 360 μl D-PBS was added per tube to obtain an LPS concentration of 200 pg/mL for the LAL assay. Each sample was then transferred into Immulon II strips (Dynatech, Chantilly, Va.) in volumes of 50 μl per well.

Figure 12:
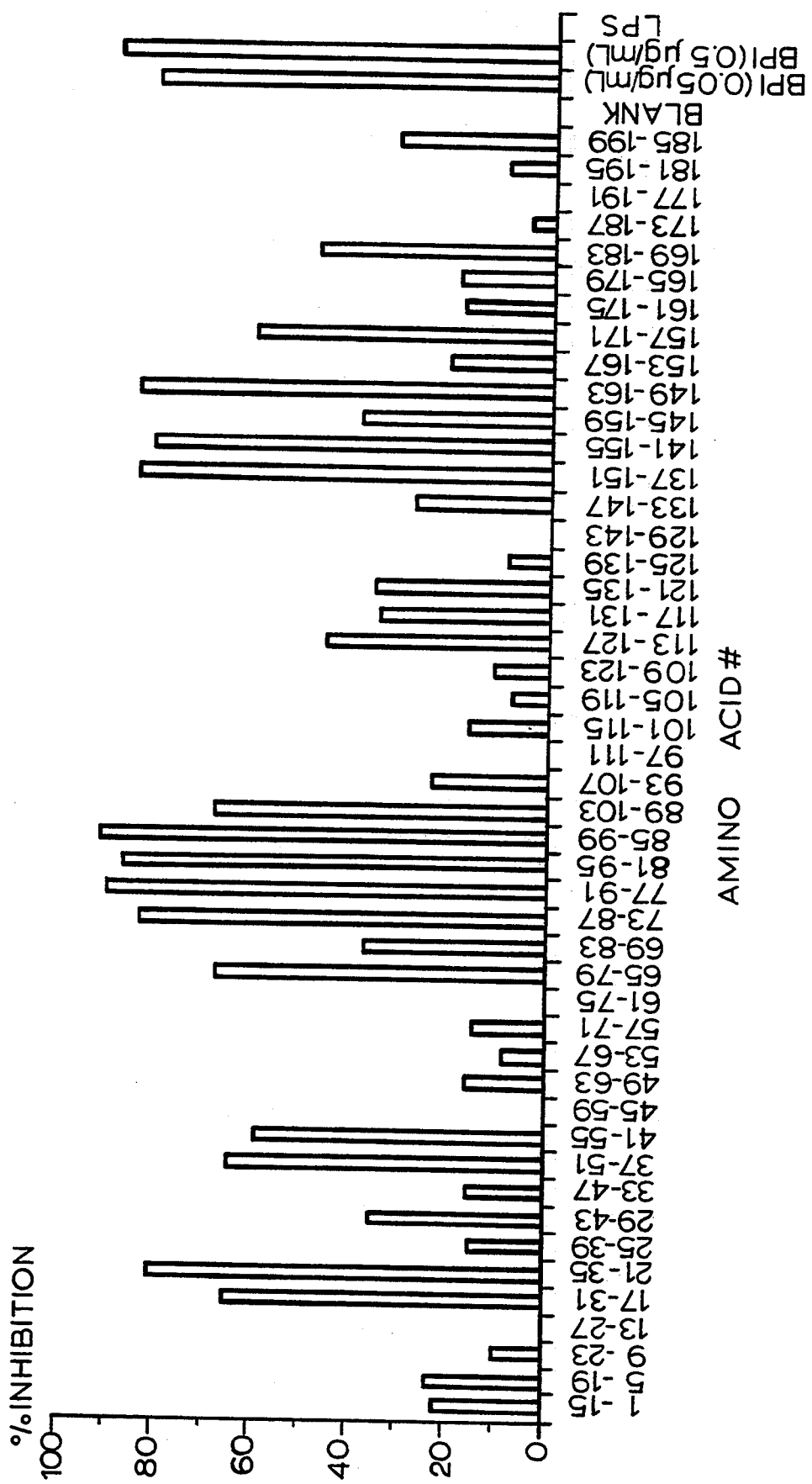
FIG. 12 depicts a graph of a Limulus Amoebocyte Lysate (LAL) inhibition assay for synthetic BPI peptides.

Limulus amoebocyte Lysate (Quantitative chromogenic LAL kit, Whitaker Bioproducts, Inc., Walkersville, Md.) was added at 50 μl per well and the wells were incubated at room temperature for 25 minutes. Chromogenic substrate was then added at a volume of 100 μl per well and was well mixed. After incubation for 20 to 30 minutes at room temperature, the reaction was stopped with addition of 100 μl of 25% acetic acid. Optical density at 405 nm was then measured in a multiplate reader (Vmax, Molecular Dynamics, Menlo Park, Calif.) with the results shown in FIG. 12 in terms of percent inhibition of LPS. The data in FIG. 12 indicate at least three major domains with significant LAL inhibition; the first extending from amino acids 17–55; the second extending from about amino acids 73–99 and the third extending from about amino acids 137–163. Other individual peptides also exhibit LAL inhibition. In contrast, material from blank control pins did not exhibit LPS neutralizing effects as measured by the LAL assay.

EXAMPLE 14

The synthetic BPI protein product peptides were tested for bactericidal effects against the rough mutant *E. coli* J5 bacteria in a radial diffusion assay. Specifically, an overnight culture of *E. Coli* J5 was diluted 1:50 into fresh tryptic soy broth and incubated for 3 hours at 37° C. to attain log phase. Bacteria were then pelleted at 3,000 rpm for 5 minutes in a Sorvall RT6000B. 5mL of 10 mM sodium phosphate buffer (ph 7.4) was added and the preparation was re-centrifuged. The supernatant was decanted and 5 mL of fresh buffer was added, the bacteria were resuspended and their concentration was determined by measurement of absorbance at 590 nm. Absorbance of $1.25 \times 10^9$ CFU/mL suspension equals 1.00. The bacteria were diluted to $4 \times 10^6$ CFU/mL in 10 mL of molten underlayer agarose (approximately 45° C.) and inverted repeatedly to mix with 15 mL polypropylene tubes used for this purpose.

The entire contents of tile tube were poured into a perfectly level square petri dish and distributed evenly by rocking the dish side to side. The agarose hardened in less than 30 seconds and had a uniform thickness of about 1 mm. A series of wells were then punched into the hardened agarose using a sterile 3 mm punch attached to a vacuum apparatus. The punch was sterilized with 100% alcohol and allowed to air dry.

10 μL of the synthetic BPI peptides were carefully pipetted into each well. As controls, pH 8.3 buffer was added to a separate well (as positive controls, 5 μg/mL and 1 μg/mL concentration of rBPI$_{23}$ was also added. In addition, products from tile blank pins B and B were tested as controls. The plate was allowed to incubate at 37° C. for 3 hours and 10 mL of molten overlayer agarose (at approximately 45° C.) was then added into the level petri dish, allowed to harden and incubated overnight at 37° C. A clear zone was seen against the lawn of bacteria in those wells having bactericidal activity. In order to visually enhance this zone, a dilute Coomassie solution (0.002% Coomassie Brilliant Blue, 27% methanol, 15% formaldehyde (37% stock solution) and H$_2$O) was poured over the agar and allowed to stain for 24 hours. The bacterial zones were measured with a Mitutoyo micrometer.

Figure 13:
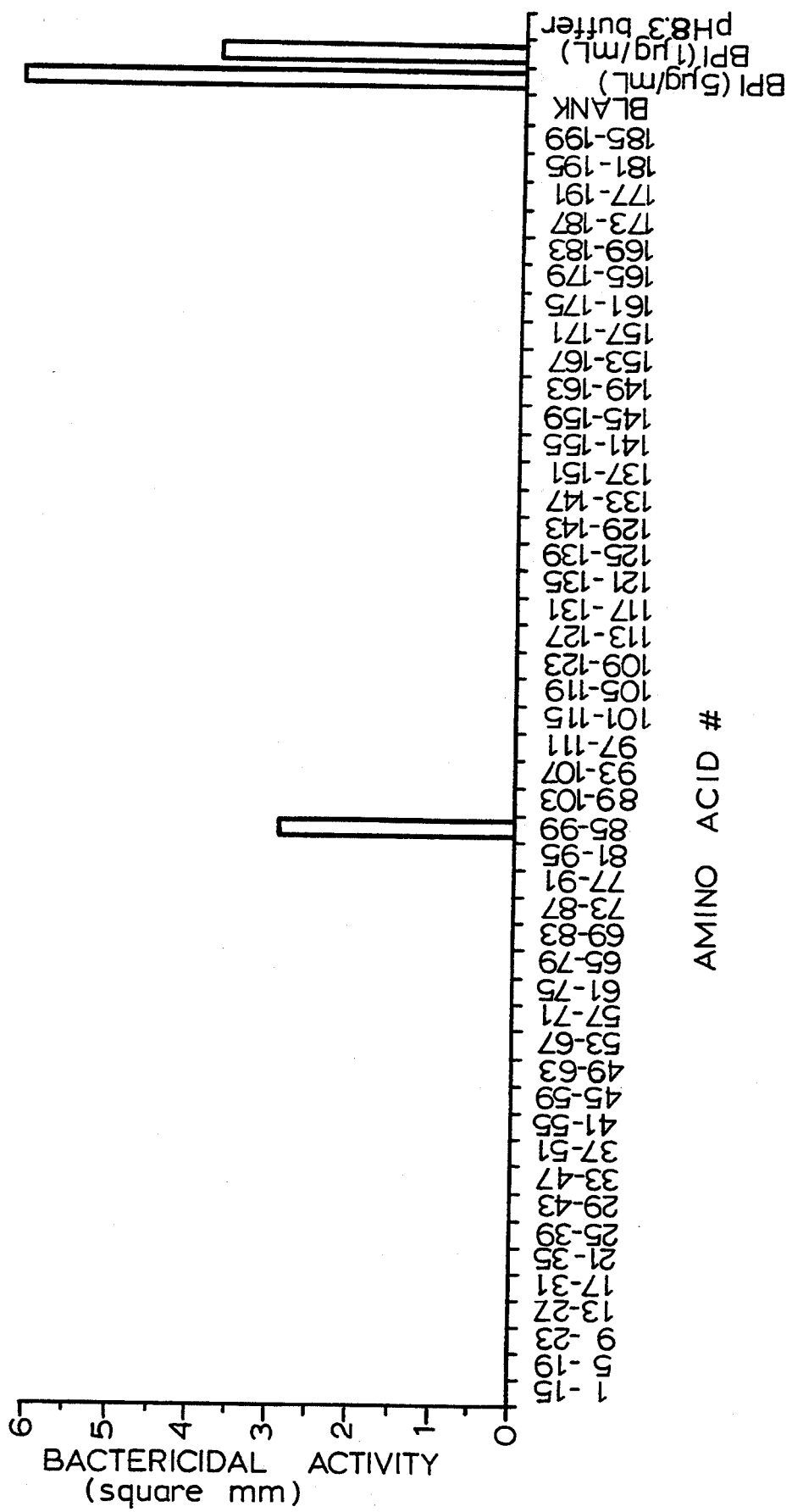
FIG. 13 depicts a graph of a radial diffusion bactericidal assay for synthetic BPI peptides.

The results of the assay are shown in FIG. 13 where the only synthetic BPI peptide seen to have bactericidal activity was a fragment corresponding to amino acids 85–99. The positive rBPI$_{23}$ controls also had bactericidal effects while the buffer and blank pin controls did not.

The results of this bactericidal assay along with the heparin binding and LAL assays indicate that there exist small synthetic BPI peptides with one or more of bactericidal, heparin binding and LPS neutralizing effects and that there exist three distinct separate functional domains within the 23 kD amino terminal fragment. The most active domain, characterized by activity in all three assays, resides between amino acids 73–99. One specific peptide 86–99 demonstrated activity in all three assays. A second domain resides between amino acid residues 25–44 and the third domain is composed of residues 117–128 and 143–163. The third domain is separated by a CSSCSS amino acid sequence that presumably is involved in a disulfide bond which brings these two minor regions in close 3-dimensional proximity within the native rBPI$_{23}$ molecule to create a third LPS/heparin binding domain.

Numerous modifications and variations in the practice of the invention are expected to occur to those skilled in the art upon consideration of the presently preferred embodiments thereof. Consequently, the only limitations which should be placed upon the scope of the invention are those which appear in the appended claims.

---

What is claimed is:

1. A method for neutralizing the anti-coagulant effect of heparin comprising administering to a subject suffering from heparin-mediated lengthening of clotting time an effective amount of a heparin binding bactericidal/permeability-increasing (BPI) protein product.

2. The method of claims claim 1 wherein the BPI protein product is a 23–25kD amino-terminal fragment of bactericidal/permeability-increasing protein.

* * * * *

UNITED STATES PATENT AND TRADEMARK OFFICE
CERTIFICATE OF CORRECTION

PATENT NO. : 5,348,942                        Page 1 of 3

DATED     : September 20, 1994

INVENTOR(S) : Roger G. Little, II, Helene Gazzano-Santoro, James B. Parent

It is certified that error appears in the above-identified patent and that said Letters Patent is hereby corrected as shown below:

Page 2 of Title page, col. 2, line 10,
Other Publications-In the title of Yayon, et al., "Basis" should be --Basic--.

Column 1, line 47 "catherization" should be --catheterization--.

Column 1, line 54 "XIIa" shoule be --XIIIa--.

Column 2, line 26 "prostglandins" should be --prostaglandins--.

Column 2, line 35 "rheumnatoid" should be --rheumatoid--.

Column 2, line 55 "is" should be --its--.

Column 3, line 22 "pyogenic" should be --pyrogenic--.

Column 3, line 46 "Bacteicidal" should be --Bactericidal--.

Column 4, line 16 "tile" should be --the--.

UNITED STATES PATENT AND TRADEMARK OFFICE
CERTIFICATE OF CORRECTION

PATENT NO. : 5,348,942

DATED : September 20, 1994

INVENTOR(S) : Roger G. Little, II, Helene Gazzano-Santoro, James B. Parent

Page 2 of 3

It is certified that error appears in the above-identified patent and that said Letters Patent is hereby corrected as shown below:

Column 4, line 21 "tile" should be --the--.

Column 4, line 47 "permeabiilty" should be --permeability--.

Column 4, line 66 "anglogenesis" should be --angiogenesis--.

Column 5, line 39 "natural synthetic" should be --natural, synthetic--.

Column 6, line 22 "grain" should be --gram--.

Column 6, line 49 "tile" should be --the--.

Column 6, line 61 "tile" should be --the--.

Column 7, line 62 "of" should be deleted.

Column 8, line 56 "were" should be --was--.

Column 9, line 6 "Aureus" should be --aureus--.

Column 9, line 13 "block" should be --blocks--.

Column 9, line 26 "$\mu$g/mL" should be --$\mu$L--.

Column 9, line 65 after "control" insert --protein--.

UNITED STATES PATENT AND TRADEMARK OFFICE
CERTIFICATE OF CORRECTION

PATENT NO. : 5,348,942

DATED : September 20, 1994

INVENTOR(S) : Roger G. Little, II, Helene Gazzano-Santoro, James B. Parent

It is certified that error appears in the above-identified patent and that said Letters Patent is hereby corrected as shown below:

Column 10, line 23 ")" should be --(--.

Column 11, line 9 "g grams" should be --grams--.

Column 12, line 24 "B16. F10" should be --B16.F10--.

Column 14, line 14 "tile" should be --the--.

Column 14, line 15 "tile" should be --the--.

Column 14, line 40 "Example 12" should be --Example 13--.

Column 14, line 41-42 "described above were" should be --were subjected to a--.

Column 14, line 47 "Addition" should be --Additional--.

Column 15, line 13 "ph" should be --pH--.

Column 15, line 23 "tile" should be --the--.

Column 15, line 34 "added" should be --added)--.

Column 15, line 35 "tile" should be --the--.

Signed and Sealed this

Fourth Day of June, 1996

BRUCE LEHMAN

Attest:

Attesting Officer

Commissioner of Patents and Trademarks